US011964098B2

(12) United States Patent
Davis et al.

(10) Patent No.: US 11,964,098 B2
(45) Date of Patent: Apr. 23, 2024

(54) AEROSOL DELIVERY DEVICE WITH A LIQUID TRANSPORT ELEMENT COMPRISING A POROUS MONOLITH AND RELATED METHOD

(71) Applicant: RAI Strategic Holdings, Inc., Winston-Salem, NC (US)

(72) Inventors: Michael F. Davis, Clemmons, NC (US); Percy D. Phillips, Pfafftown, NC (US); James W. Rogers, Cornelius, NC (US); Frederic P. Ampolini, Winston-Salem, NC (US); David A. Clemens, Chapel Hill, NC (US); William K. Carpenter, Warrensville, NC (US); Owen L. Joyce, Cary, NC (US); Michael L. King, Durham, NC (US); Sean M. Ahr, Raleigh, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 137 days.

(21) Appl. No.: 16/822,864

(22) Filed: Mar. 18, 2020

(65) Prior Publication Data

US 2020/0214348 A1    Jul. 9, 2020

Related U.S. Application Data

(63) Continuation of application No. 15/216,582, filed on Jul. 21, 2016, now Pat. No. 10,617,151.

(51) Int. Cl.
*A61M 15/06*    (2006.01)
*A24F 40/44*    (2020.01)
(Continued)

(52) U.S. Cl.
CPC ............. *A61M 15/06* (2013.01); *A24F 40/44* (2020.01); *A61M 11/042* (2014.02); *F22B 1/284* (2013.01);
(Continued)

(58) Field of Classification Search
CPC .......... A24F 40/10; A24F 40/44; A24F 40/46; A24F 40/70; A61M 11/042; A61M 15/06;
(Continued)

(56) References Cited

U.S. PATENT DOCUMENTS 1,771,366 A    7/1930    Wyss et al.
2,057,353 A    10/1936   Whittemore, Jr.
(Continued)

FOREIGN PATENT DOCUMENTS

AU           276250        7/1965
CA         2 641 869       5/2010
(Continued)

OTHER PUBLICATIONS

Partial International Search Report, PCT/IB2017/054380, dated Nov. 17, 2017.
(Continued)

*Primary Examiner* — Sang Y Paik
(74) *Attorney, Agent, or Firm* — Womble Bond Dickinson (US) LLP

(57) ABSTRACT

The present disclosure relates to aerosol delivery devices, methods of producing such devices, and elements of such devices. In some embodiments, the present disclosure provides devices configured for vaporization of an aerosol precursor composition that is contained in a reservoir and transported to a heating element by a liquid transport element. The liquid transport element may include a porous monolith.

8 Claims, 22 Drawing Sheets

(51) Int. Cl.
*A61M 11/04* (2006.01)
*F22B 1/28* (2006.01)
*H01B 1/02* (2006.01)
*H05B 1/02* (2006.01)
*H05B 3/44* (2006.01)
*A24F 40/10* (2020.01)
*A24F 40/46* (2020.01)
*A24F 40/70* (2020.01)
*A61M 16/00* (2006.01)

(52) U.S. Cl.
CPC ............ *H05B 1/0297* (2013.01); *H05B 3/44* (2013.01); *A24F 40/10* (2020.01); *A24F 40/46* (2020.01); *A24F 40/70* (2020.01); *A61M 2016/0024* (2013.01); *A61M 2205/502* (2013.01); *A61M 2205/581* (2013.01); *A61M 2205/582* (2013.01); *A61M 2205/587* (2013.01); *A61M 2205/8206* (2013.01); *A61M 2205/8237* (2013.01)

(58) Field of Classification Search
CPC .... A61M 2016/0024; A61M 2205/502; A61M 2205/581; A61M 2205/582; A61M 2205/587; A61M 2205/8206; A61M 2205/8237; F22B 1/284; H05B 1/0297; H05B 3/44
USPC .................................................. 392/386–406
See application file for complete search history.

(56) References Cited

U.S. PATENT DOCUMENTS

| | | |
|---|---|---|
| 2,104,266 A | 1/1938 | McCormick |
| 2,547,865 A * | 4/1951 | Hanks ..................... H05B 3/00 392/338 |
| 3,200,819 A | 8/1965 | Gilbert |
| 4,284,089 A | 8/1981 | Ray |
| 4,303,083 A | 12/1981 | Burruss, Jr. |
| 4,419,302 A | 12/1983 | Nishino et al. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,068 B2 | 10/2013 | Terry et al. |
| 8,550,069 B2 | 10/2013 | Alelov |
| 8,746,240 B2 | 6/2014 | Terry et al. |
| 8,757,147 B2 | 6/2014 | Terry et al. |
| 8,851,081 B2 | 10/2014 | Fernando et al. |
| 9,095,175 B2 | 8/2015 | Terry et al. |
| 9,259,035 B2 | 2/2016 | Terry et al. |
| 10,194,693 B2 | 2/2019 | Wensley et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |

(56) References Cited

U.S. PATENT DOCUMENTS

| | | | |
|---|---|---|---|
| 2011/0036363 | A1 | 2/2011 | Urtsev et al. |
| 2011/0036365 | A1 | 2/2011 | Chong et al. |
| 2011/0094523 | A1 | 4/2011 | Thorens et al. |
| 2011/0126848 | A1 | 6/2011 | Zuber et al. |
| 2011/0155153 | A1 | 6/2011 | Thorens et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0277780 | A1 | 11/2011 | Terry et al. |
| 2011/0309157 | A1 | 12/2011 | Yang et al. |
| 2012/0042885 | A1 | 2/2012 | Stone et al. |
| 2012/0060853 | A1 | 3/2012 | Robinson et al. |
| 2012/0111347 | A1 | 5/2012 | Hon |
| 2012/0132643 | A1 | 5/2012 | Choi et al. |
| 2012/0227752 | A1 | 9/2012 | Alelov |
| 2012/0231464 | A1 | 9/2012 | Yu et al. |
| 2012/0260927 | A1 | 10/2012 | Liu |
| 2012/0279512 | A1 | 11/2012 | Hon |
| 2012/0318882 | A1 | 12/2012 | Abehasera |
| 2013/0037041 | A1 | 2/2013 | Worm et al. |
| 2013/0056013 | A1 | 3/2013 | Terry et al. |
| 2013/0081625 | A1 | 4/2013 | Rustad et al. |
| 2013/0081642 | A1 | 4/2013 | Safari |
| 2013/0087160 | A1 | 4/2013 | Gherghe |
| 2013/0192619 | A1 | 8/2013 | Tucker et al. |
| 2013/0192623 | A1 | 8/2013 | Tucker et al. |
| 2013/0255702 | A1 | 10/2013 | Griffith, Jr. et al. |
| 2013/0306084 | A1 | 11/2013 | Flick |
| 2013/0319439 | A1 | 12/2013 | Gorelick et al. |
| 2013/0340750 | A1 | 12/2013 | Thorens et al. |
| 2013/0340775 | A1 | 12/2013 | Juster et al. |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0109921 | A1 | 4/2014 | Chen |
| 2014/0123989 | A1 | 5/2014 | LaMothe |
| 2014/0157583 | A1 | 6/2014 | Ward et al. |
| 2014/0209105 | A1 | 7/2014 | Sears et al. |
| 2014/0246020 | A1 | 9/2014 | Minskoff et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2014/0345631 | A1 | 11/2014 | Bowen et al. |
| 2015/0007838 | A1 | 1/2015 | Fernando et al. |
| 2015/0053217 | A1 | 2/2015 | Steingraber et al. |
| 2015/0090280 | A1 | 4/2015 | Chen |
| 2015/0144145 | A1 | 5/2015 | Chang et al. |
| 2015/0245669 | A1 | 9/2015 | Cadieux et al. |
| 2015/0272218 | A1 | 10/2015 | Chen |
| 2016/0021930 | A1* | 1/2016 | Minskoff ................ A24F 40/51 392/395 |
| 2016/0037826 | A1 | 2/2016 | Hearn et al. |
| 2016/0128386 | A1 | 5/2016 | Chen |
| 2017/0347714 | A1* | 12/2017 | Metz ...................... A24F 40/46 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 101843368 | 9/2010 |
| CN | 203748667 | 8/2014 |
| CN | 204994617 | 1/2016 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| GB | 2504075 | 1/2014 |
| GB | 2513637 | 11/2014 |
| GB | 2529201 A | 2/2016 |
| RU | 107026 | 8/2011 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2011/042212 | 4/2011 |
| WO | WO 2011/146175 | 11/2011 |
| WO | WO 2012/072762 | 6/2012 |
| WO | WO 2012/100523 | 8/2012 |
| WO | WO 2013/089551 | 6/2013 |
| WO | WO 2014/012905 | 1/2014 |
| WO | WO 2014/012906 | 1/2014 |
| WO | WO-2015114327 A1 | 8/2015 |

OTHER PUBLICATIONS

International Search Report, PCT/IB2017/054380, dated May 4, 2018.

European Patent Office, Extended European Search Report for EP Application No. 22212889.4, dated Mar. 23, 2023, pp. 1-11.

* cited by examiner

| CONTAIN AN AEROSOL PRECURSOR COMPOSITION IN A UNITARY RESERVOIR AND LIQUID TRANSPORT ELEMENT | ~ 602 |

↓

| VAPORIZE AT LEAST A PORTION OF THE AEROSOL PRECURSOR COMPOSITION AT THE UNITARY RESERVOIR AND LIQUID TRANSPORT ELEMENT | ~ 604 |

*FIG. 13*

| POSITION A HEATING ELEMENT, A RESERVOIR AND A LIQUID TRANSPORT ELEMENT IN AN OUTER BODY SUCH THAT THE LIQUID TRANSPORT ELEMENT IS IN CONTACT WITH THE RESERVOIR AND THE HEATING ELEMENT | —1102 |

↓

| ALIGN A RESPECTIVE LONGITUDINAL AXIS OF THE HEATING ELEMENT, THE RESERVOIR AND THE LIQUID TRANSPORT ELEMENT | —1104 |

FIG. 23

AEROSOL DELIVERY DEVICE WITH A LIQUID TRANSPORT ELEMENT COMPRISING A POROUS MONOLITH AND RELATED METHOD

CROSS-REFERENCE TO RELATED APPLICATIONS

This application is a continuation of U.S. application Ser. No. 15/216,582, filed on Jul. 21, 2016, which application is hereby incorporated by reference in its entirety in this application.

BACKGROUND

Field of the Disclosure

The present disclosure relates to aerosol delivery devices, and more particularly to aerosol delivery devices that may utilize electrically generated heat for the production of aerosol (e.g., commonly referred to as electronic cigarettes). The aerosol delivery devices may be configured to heat an aerosol precursor, which may incorporate materials that may be made or derived from tobacco or otherwise incorporate tobacco, the precursor being capable of forming an inhalable substance for human consumption.

Description of Related Art

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., which are incorporated herein by reference. See also, for example, the various types of articles, aerosol delivery devices, and electrically powered heat generating sources referenced by brand name and commercial source in U.S. Pat. Pub. No. 2015/0216236 to Bless et al., which is incorporated herein by reference.

It would be desirable to provide a reservoir and a liquid transport element for an aerosol precursor composition for use in an aerosol delivery device, the reservoir and the liquid transport element being provided so as to improve formation of the aerosol delivery device. It would also be desirable to provide aerosol delivery devices that are prepared to utilize such reservoirs and liquid transport elements.

BRIEF SUMMARY OF THE DISCLOSURE

The present disclosure relates to aerosol delivery devices configured to produce aerosol and which aerosol delivery devices, in some embodiments, may be referred to as electronic cigarettes. In one aspect, an aerosol delivery device is provided. The aerosol delivery device may include an outer body. A heating element and a reservoir may be received in the outer body. A liquid transport element may be at least partially received within the reservoir and may be engaged with the heating element. The liquid transport element may include a porous monolith.

In some embodiments a longitudinal axis of the heating element may be substantially parallel to a longitudinal axis of the outer body. The porous monolith may include at least one of a porous ceramic and a porous glass. The aerosol delivery device may further include a first heating terminal and a second heating terminal coupled to the heating element. The first heating terminal and the second heating terminal may be positioned between the liquid transport element and the reservoir.

In some embodiments the liquid transport element may define one or more channels extending at least partially therethrough. The heating element may be at least partially received in the one or more channels. The aerosol delivery device may further include a first heating terminal and a second heating terminal coupled to the heating element and at least partially received in the one or more channels. Additionally, the aerosol delivery device may include an electronic component at least partially received in the one or more channels. The electronic component may be positioned between the first heating terminal and the second heating terminal. A longitudinal axis of the electronic component may extend substantially parallel to a longitudinal axis of the outer body.

In some embodiments the liquid transport element may extend at least partially about the liquid transport element. The aerosol delivery device may further include a flow director. The flow director may define a longitudinal axis extending substantially parallel to a longitudinal axis of the liquid transport element.

In some embodiments the aerosol delivery device may further include a base engaged with the outer body and an electronic component positioned between the reservoir and the base. A longitudinal axis of the electronic component may extend substantially perpendicular to a longitudinal axis of the outer body. Additionally, the aerosol delivery device may include a first heating terminal and a second heating terminal coupled to the heating element. The first heating terminal and the second heating terminal may extend substantially perpendicular to the longitudinal axis of the electronic component.

In an additional aspect a method for producing an aerosol delivery device is provided. The method may include positioning a heating element, a reservoir and a liquid transport element in an outer body such that the liquid transport element is in contact with the reservoir and the heating element. Positioning the heating element, the reservoir and the liquid transport element in the outer body may include aligning a respective longitudinal axis of the heating element, the reservoir and the liquid transport element.

In some embodiments the method may further include positioning the liquid transport element at least partially within the reservoir. Positioning the liquid transport element at least partially within the reservoir may include wrapping the liquid transport element with the reservoir. Additionally, the method may include inserting the heating element into a channel extending at least partially though the liquid transport element. The method may further include coupling the heating element an outer surface of the liquid transport element.

These and other features, aspects, and advantages of the disclosure will be apparent from a reading of the following detailed description together with the accompanying drawings, which are briefly described below.

BRIEF DESCRIPTION OF THE FIGURES

Figure 1:
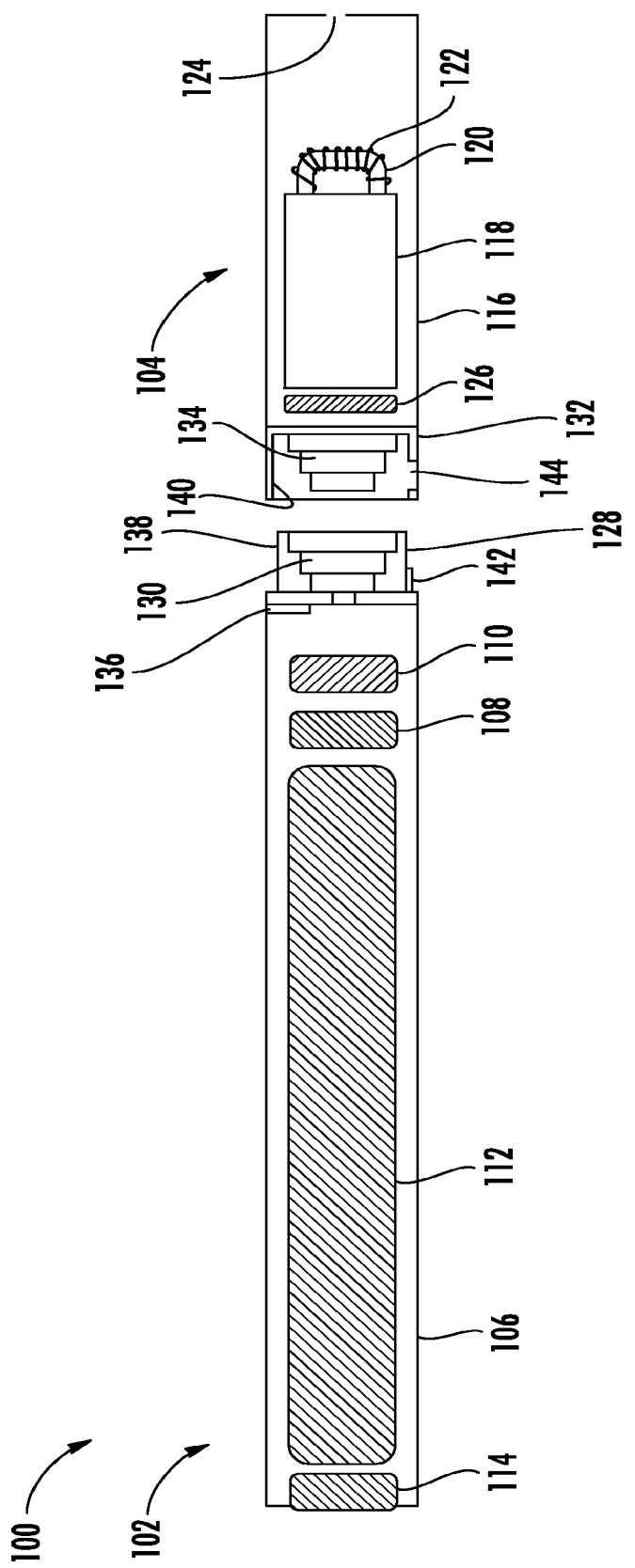
Figure 2:
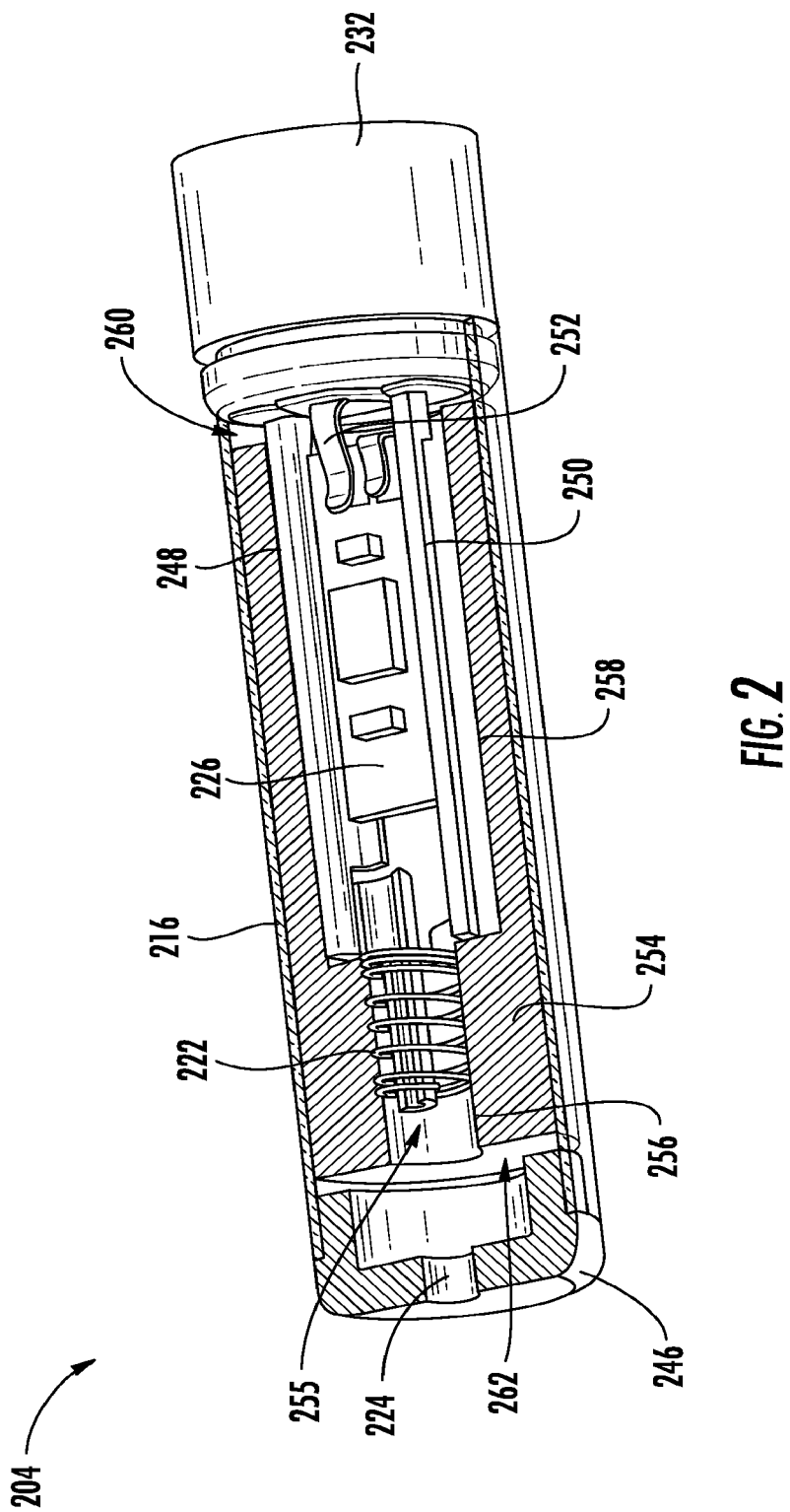
Figure 3:
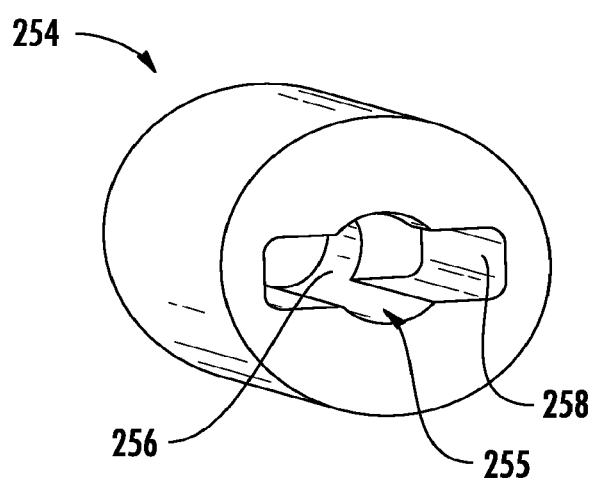
Figure 4:
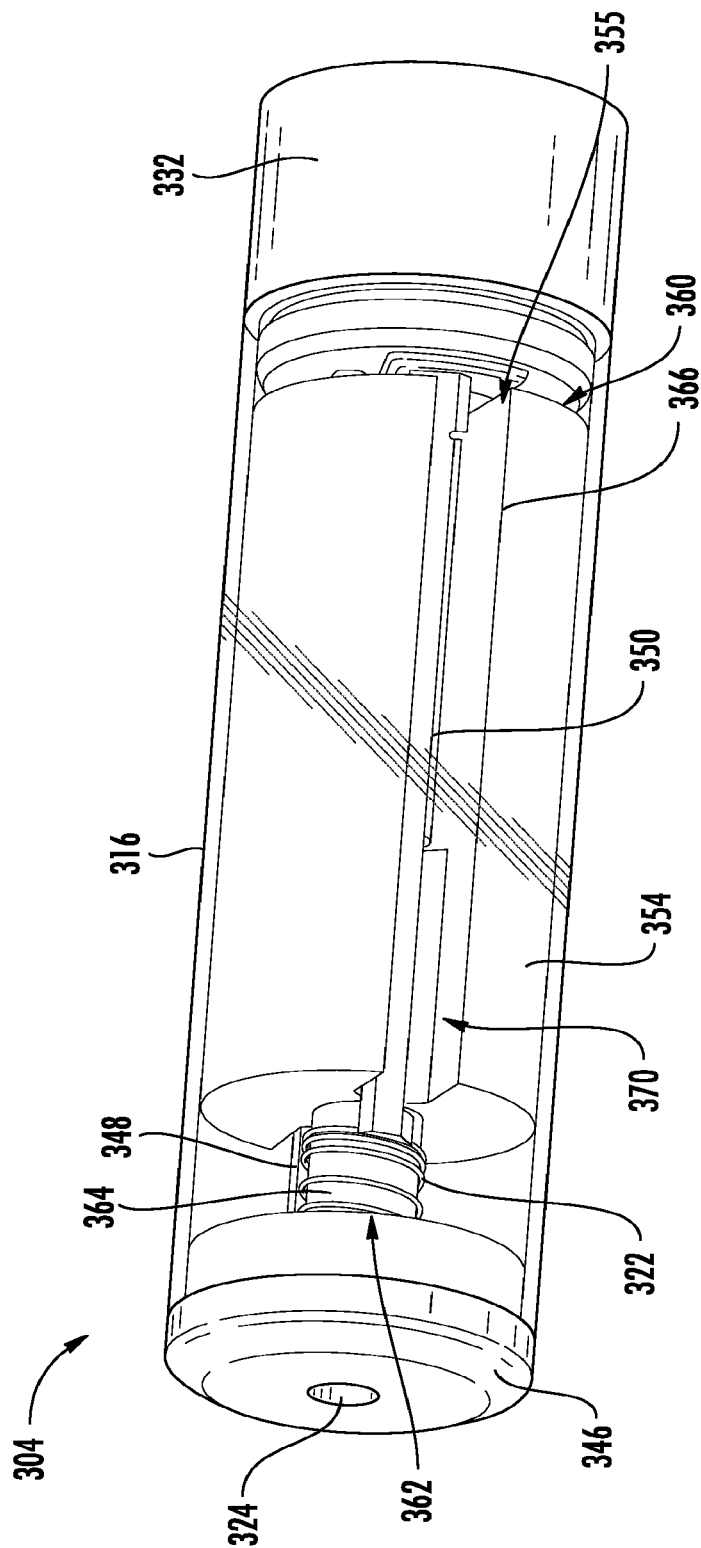
Figure 5:
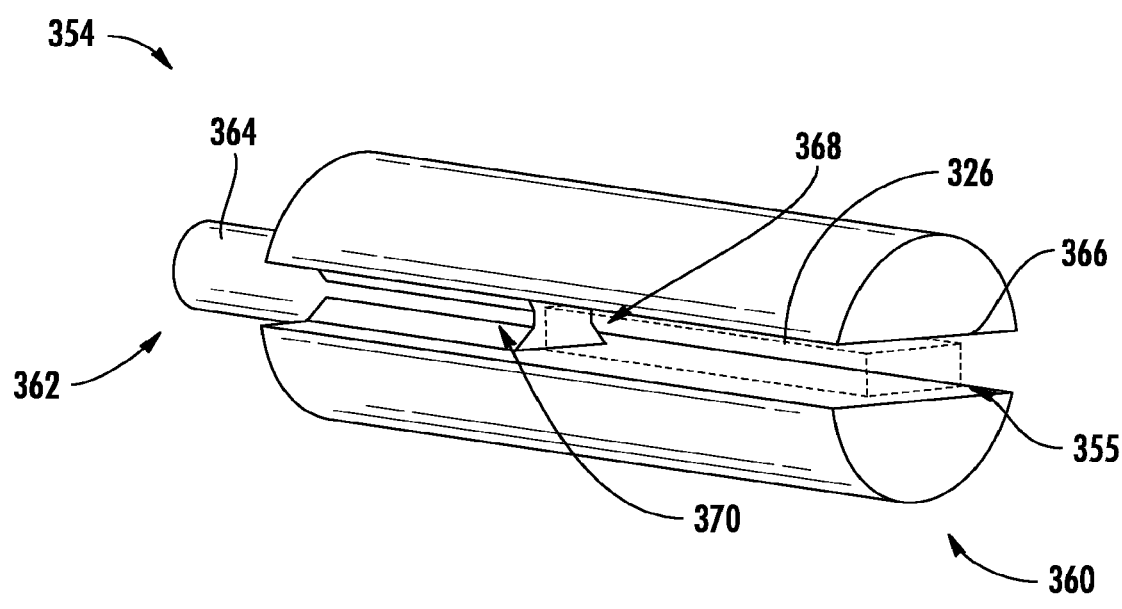
Figure 6:
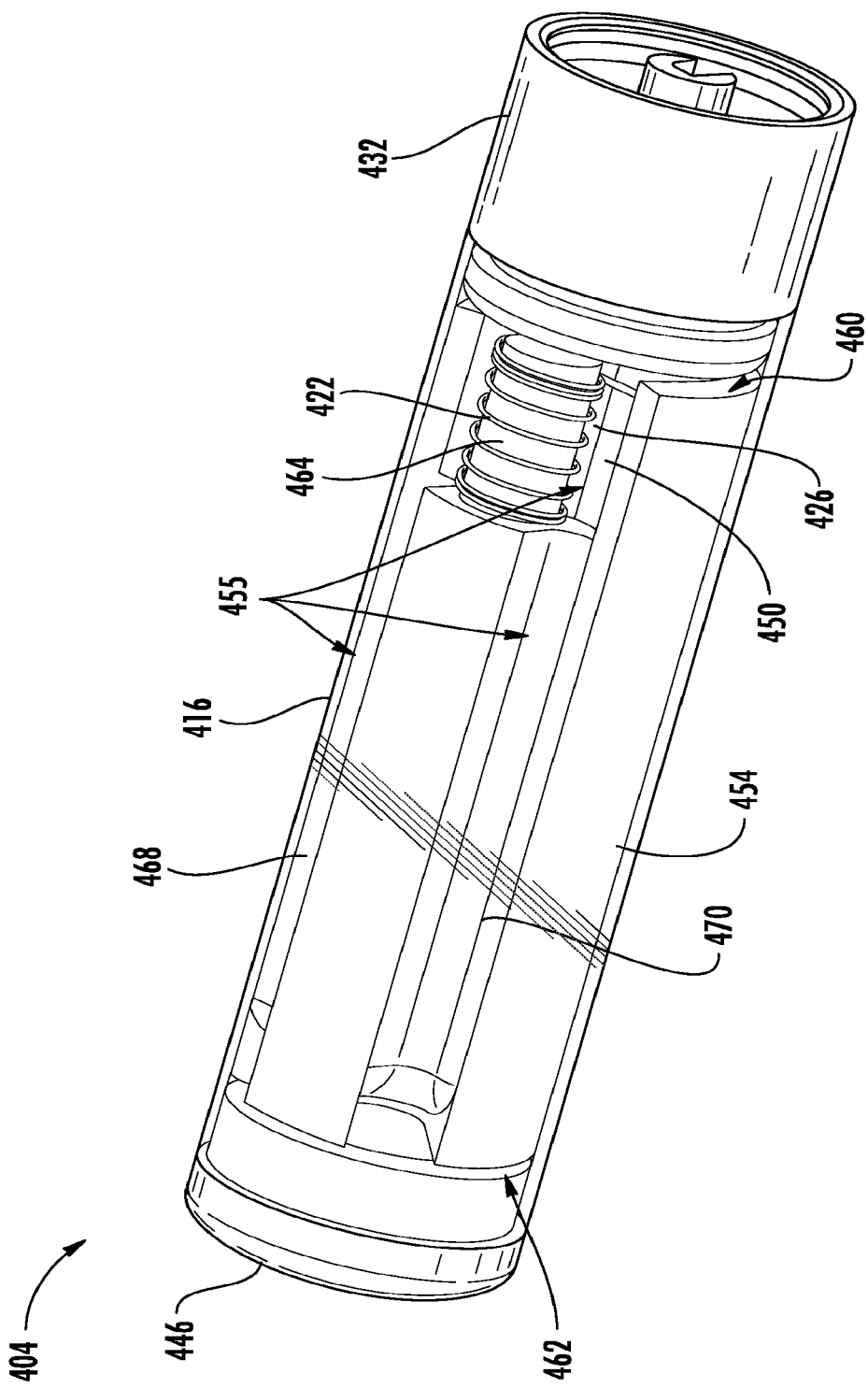
Figure 7:
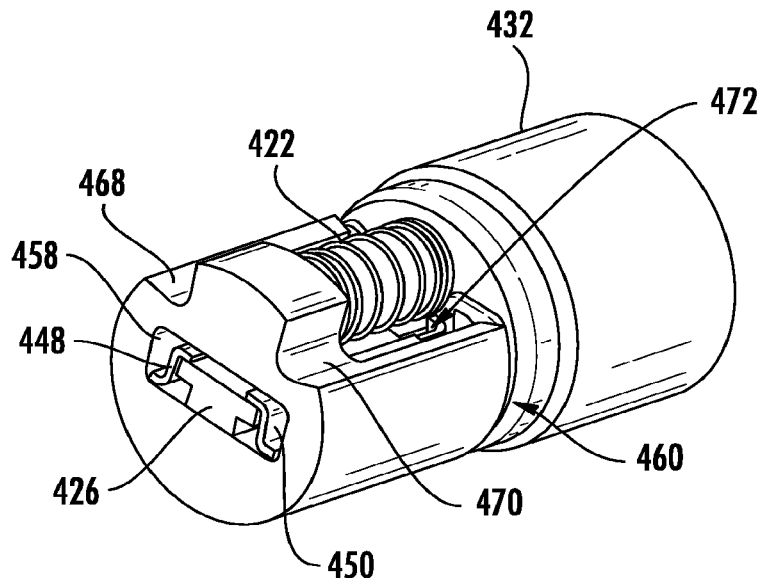
Figure 8:
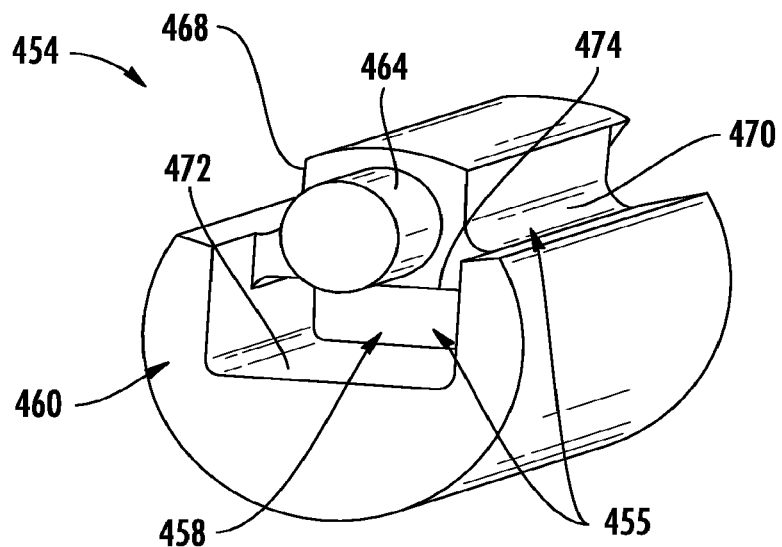
Figure 9:
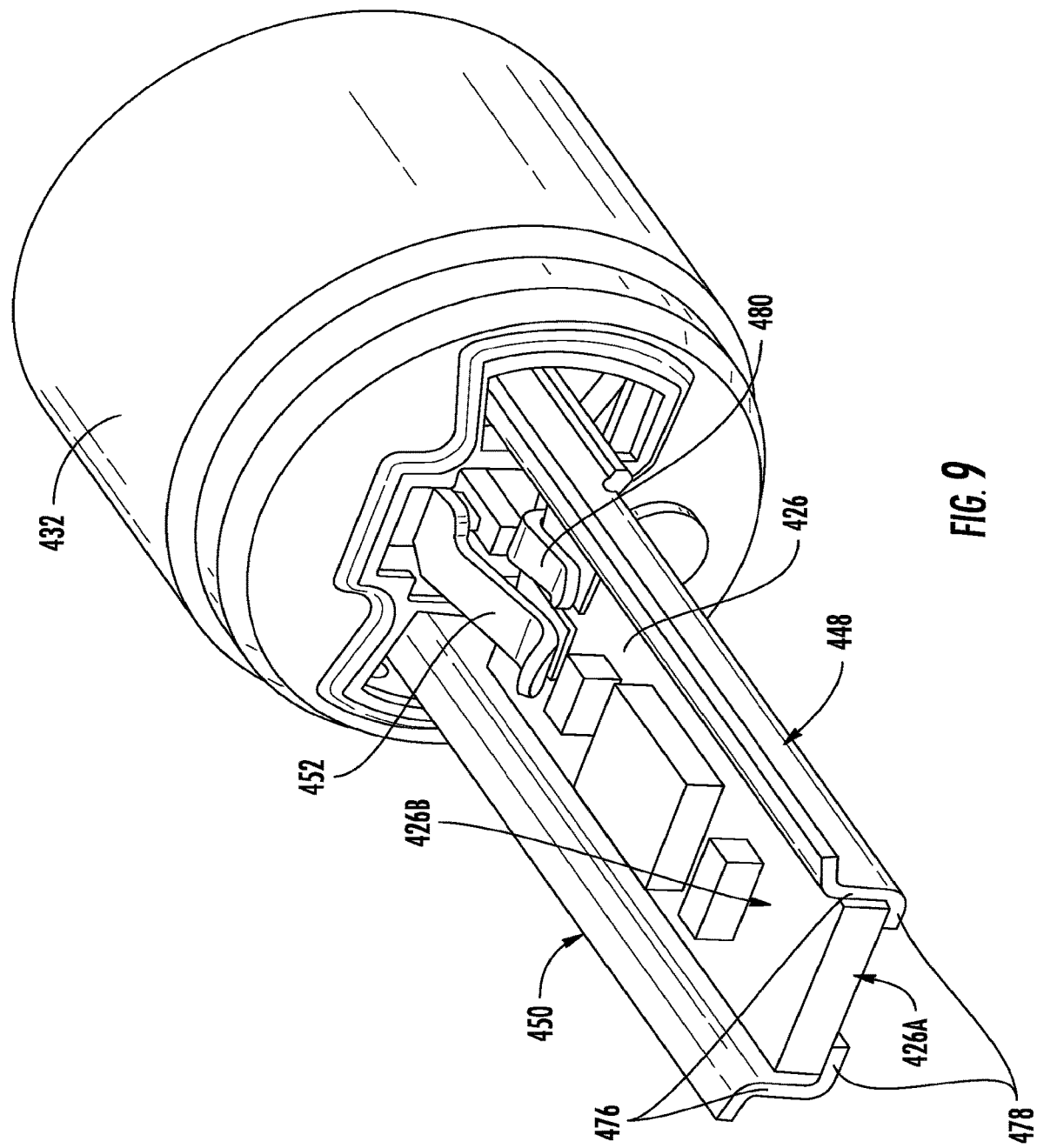
Figure 10:
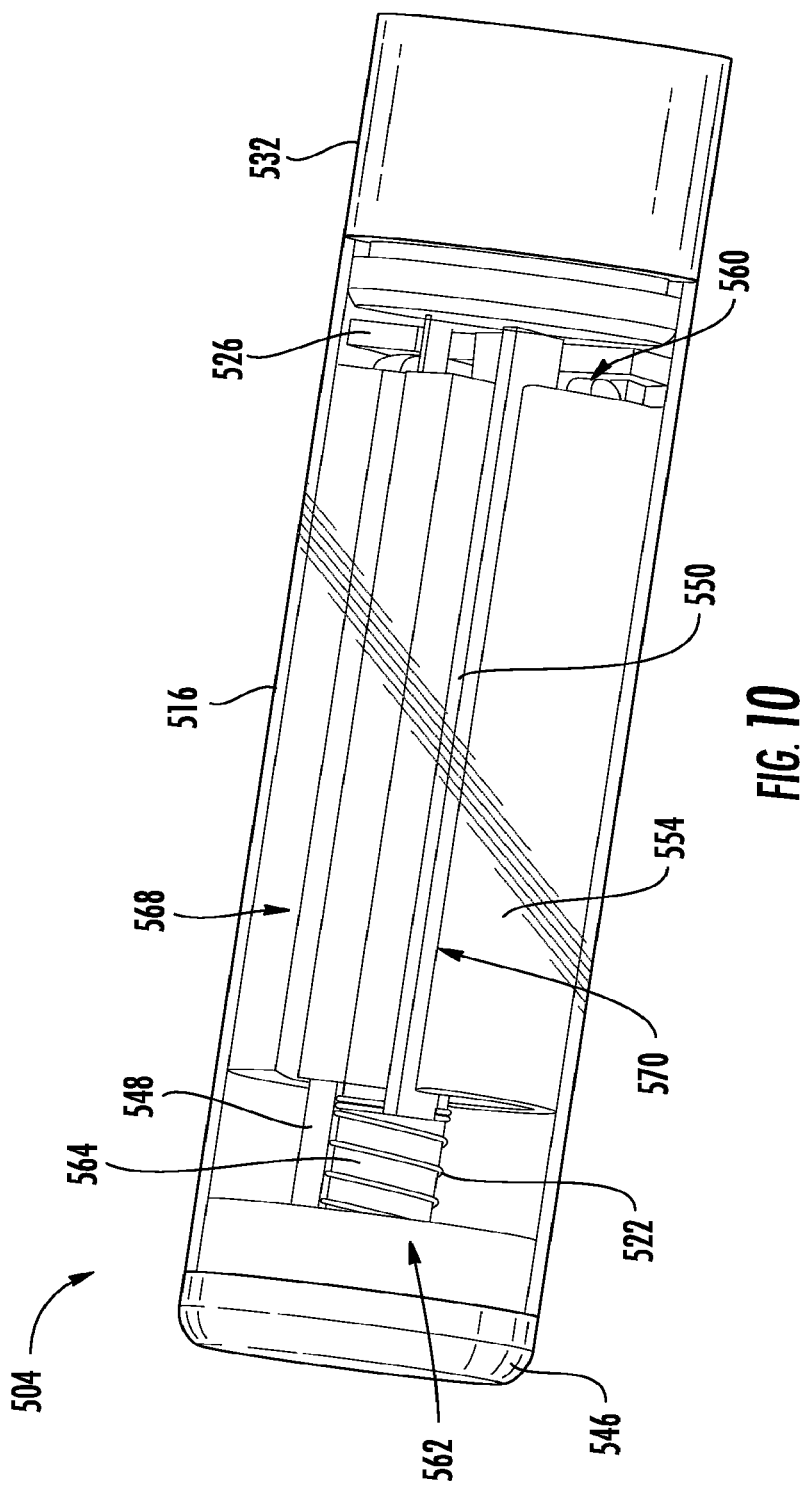
Figure 11:
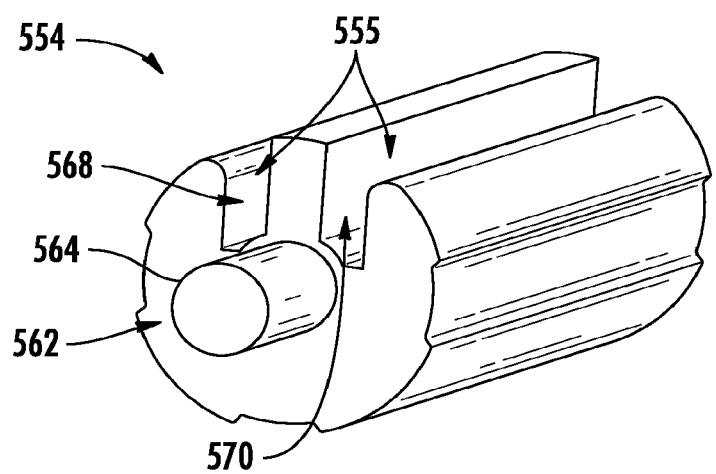
Figure 12:
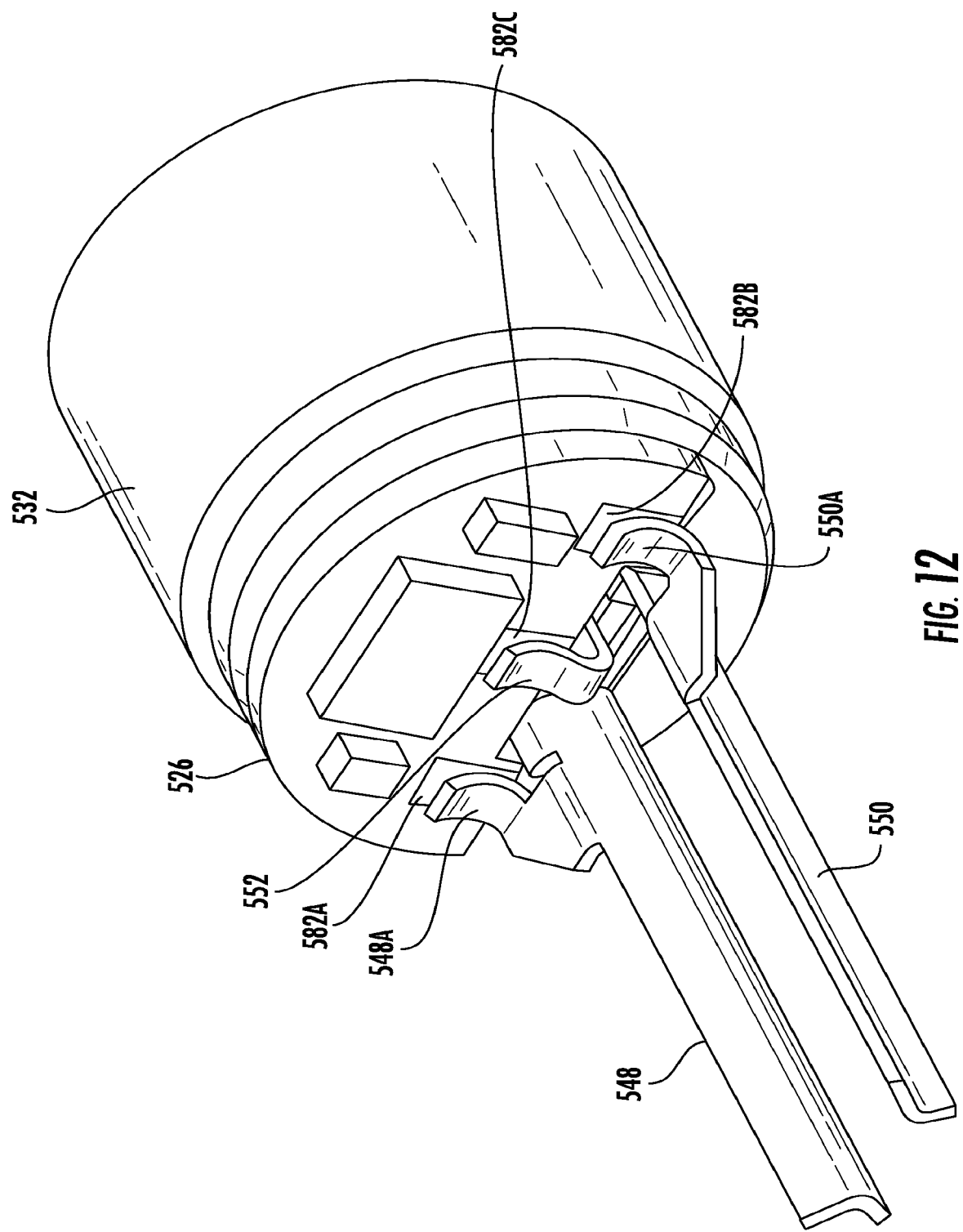
Figure 14:
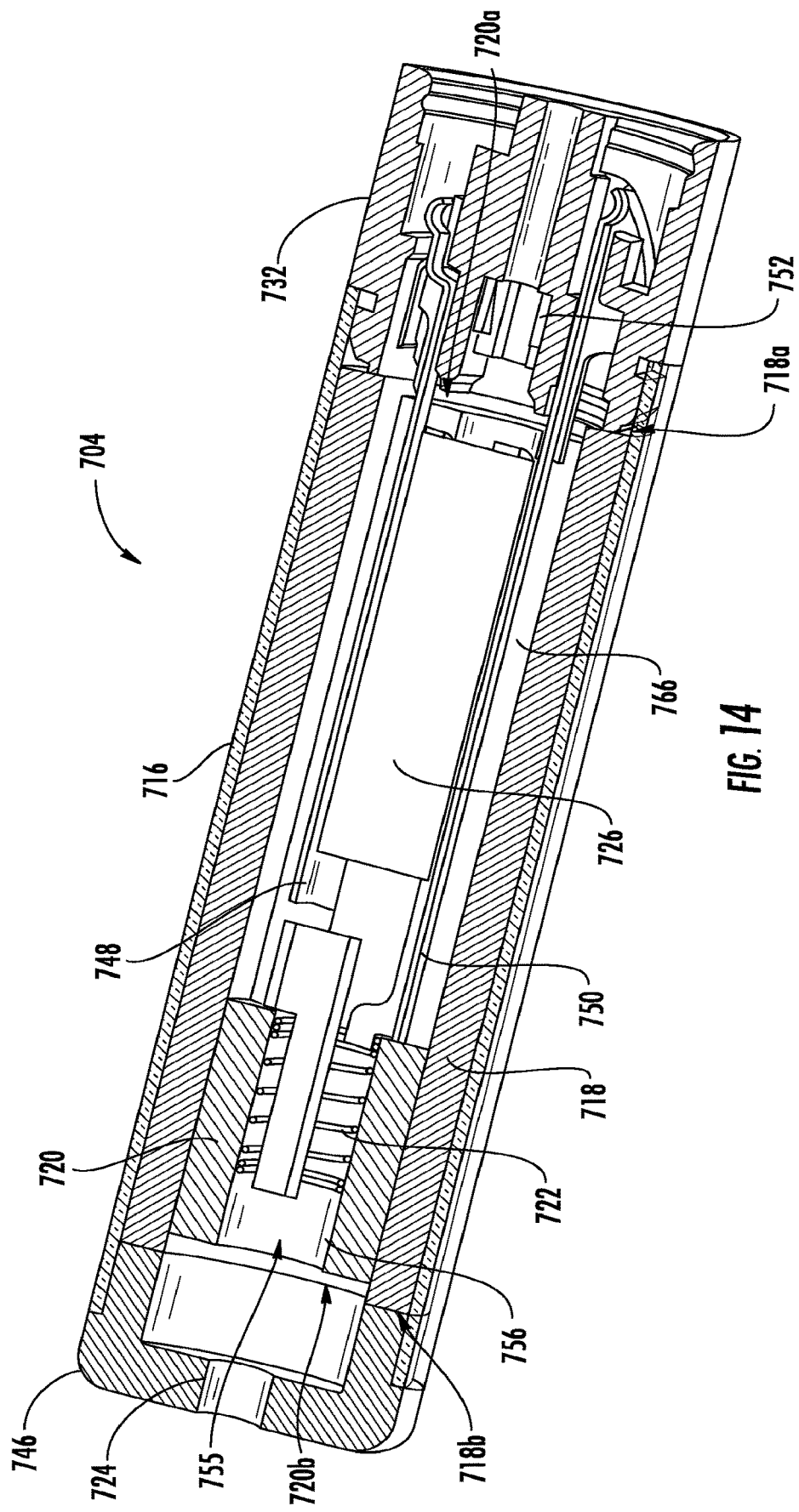
Figure 15:
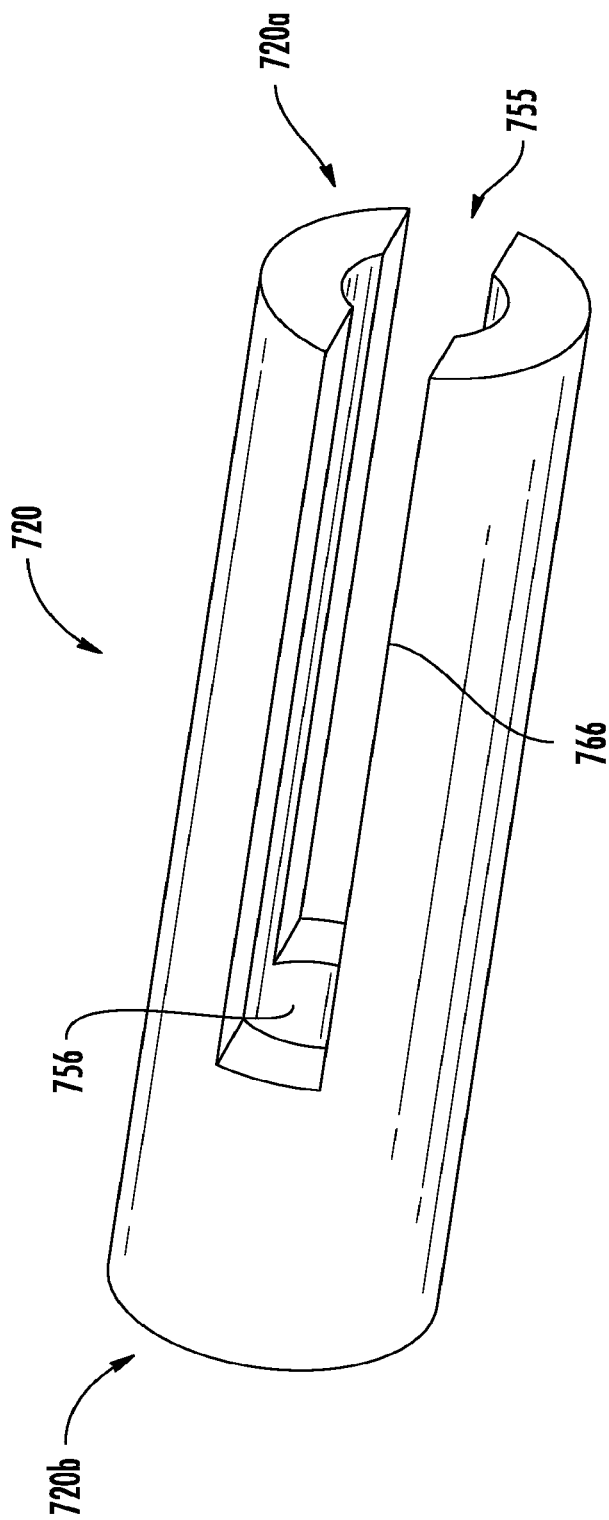
Figure 16:
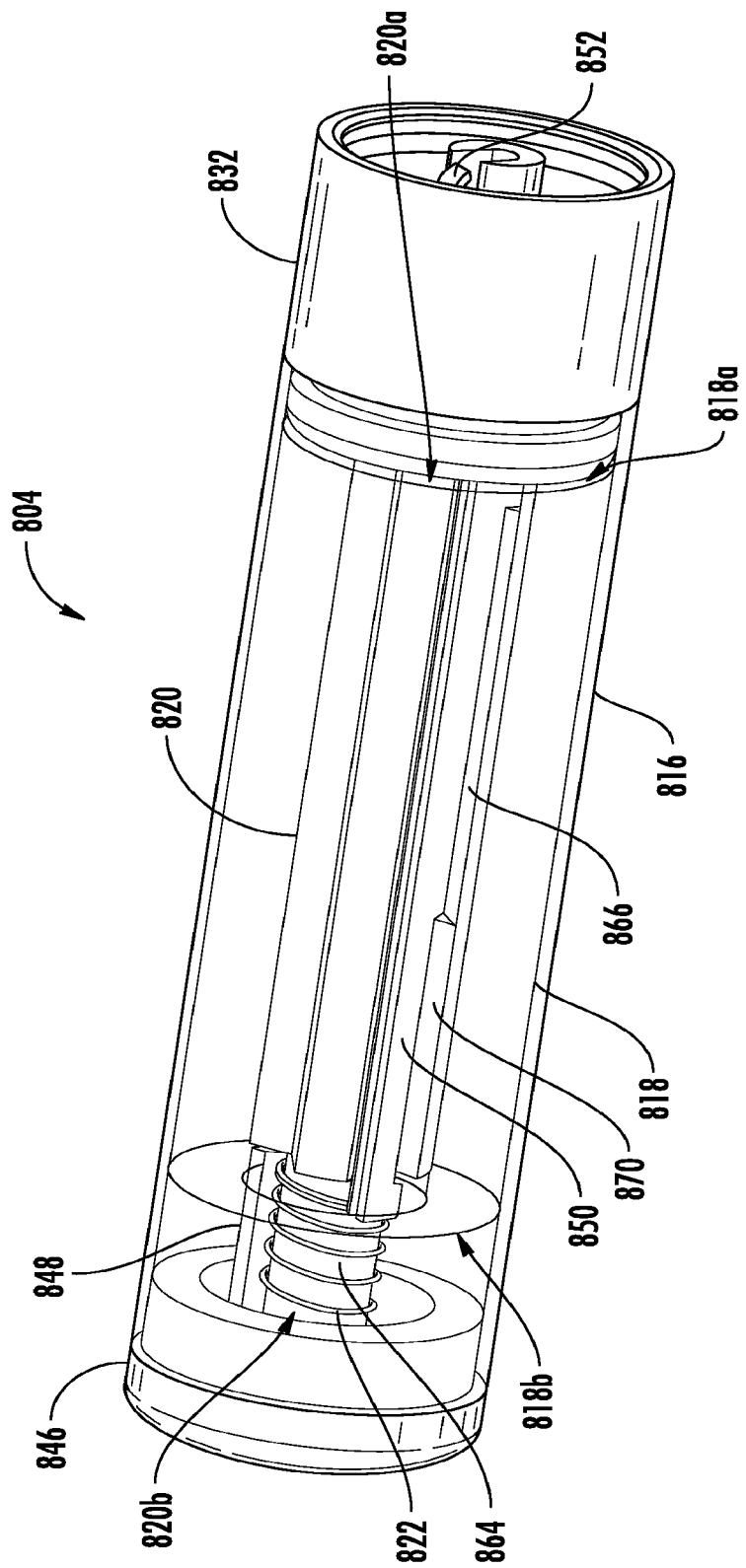
Figure 17:
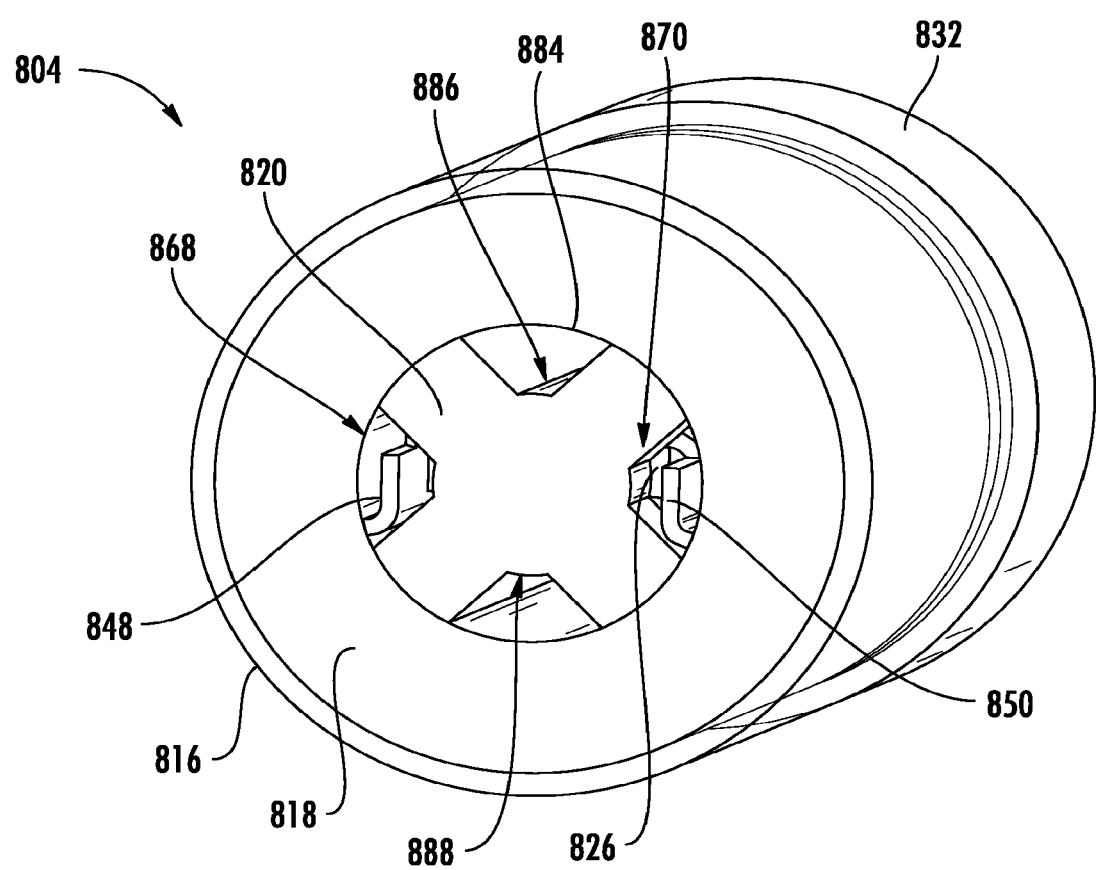
Figure 18:
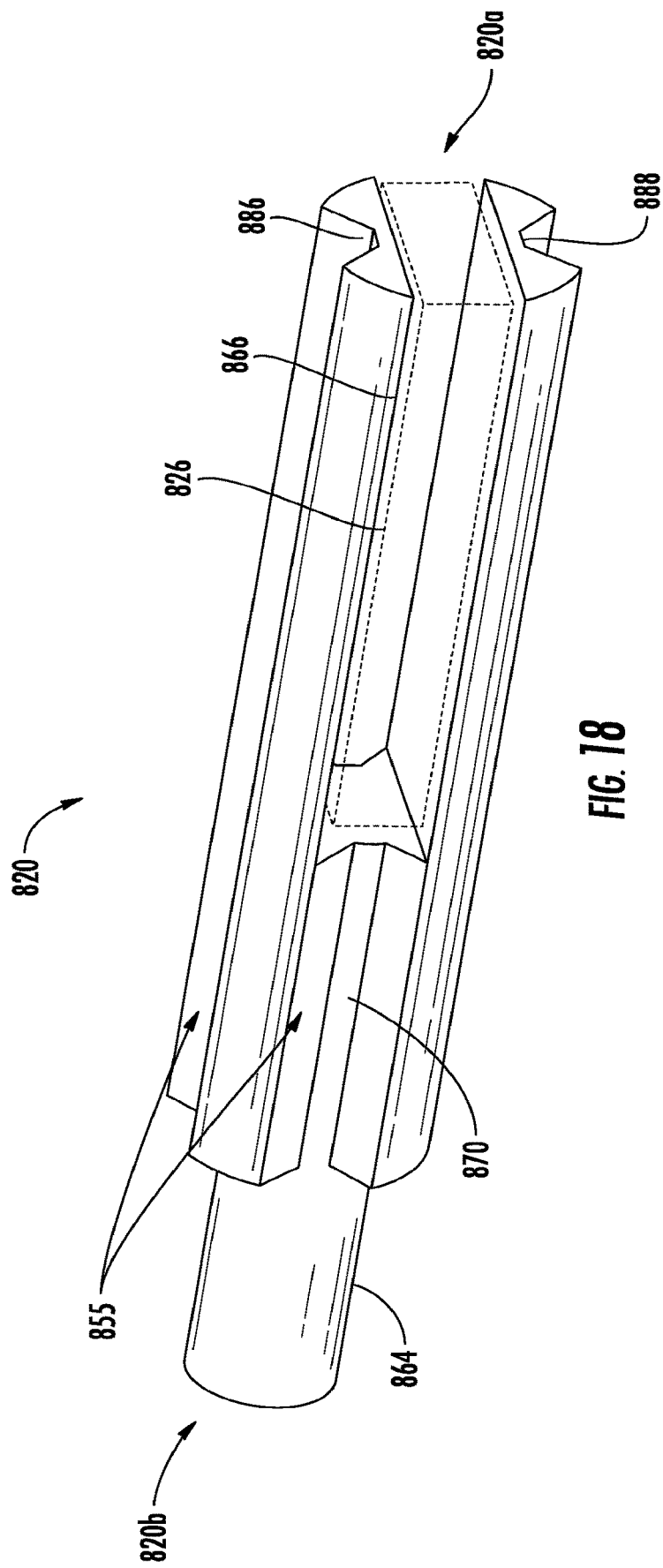
Figure 19:
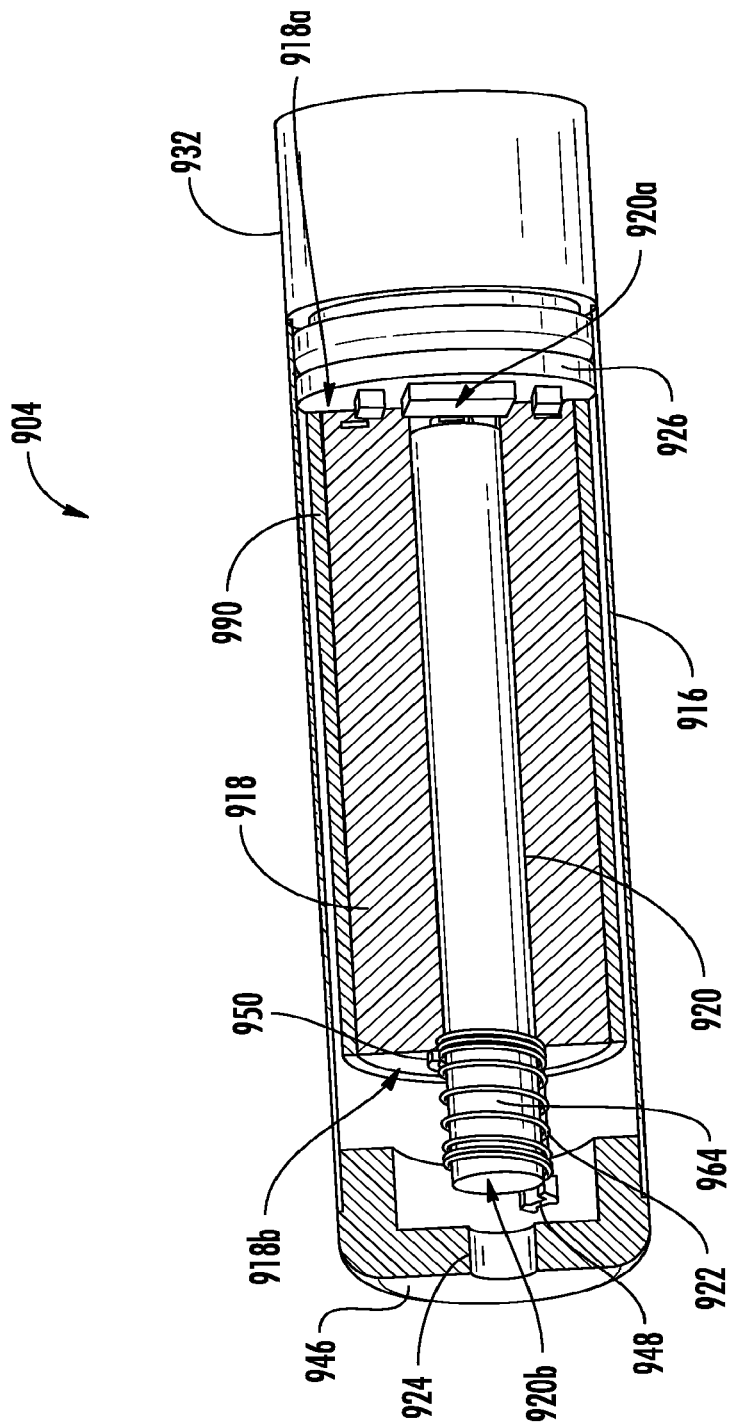
Figure 20:
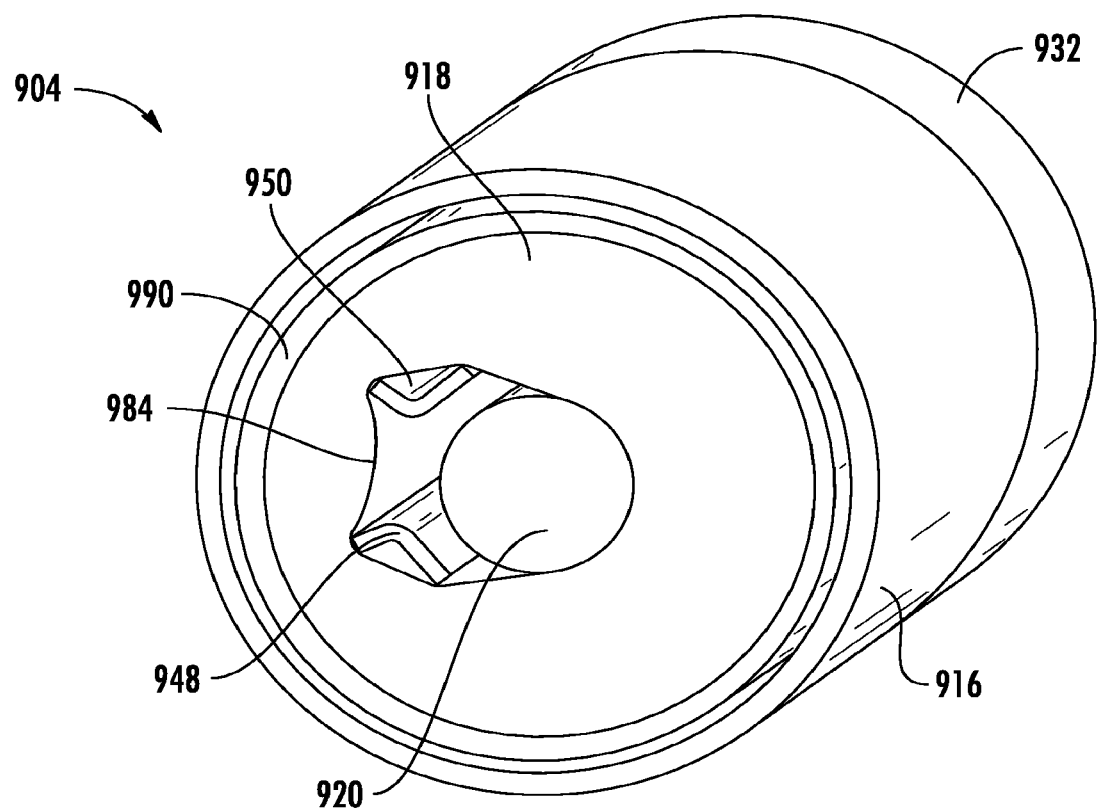
Figure 21:
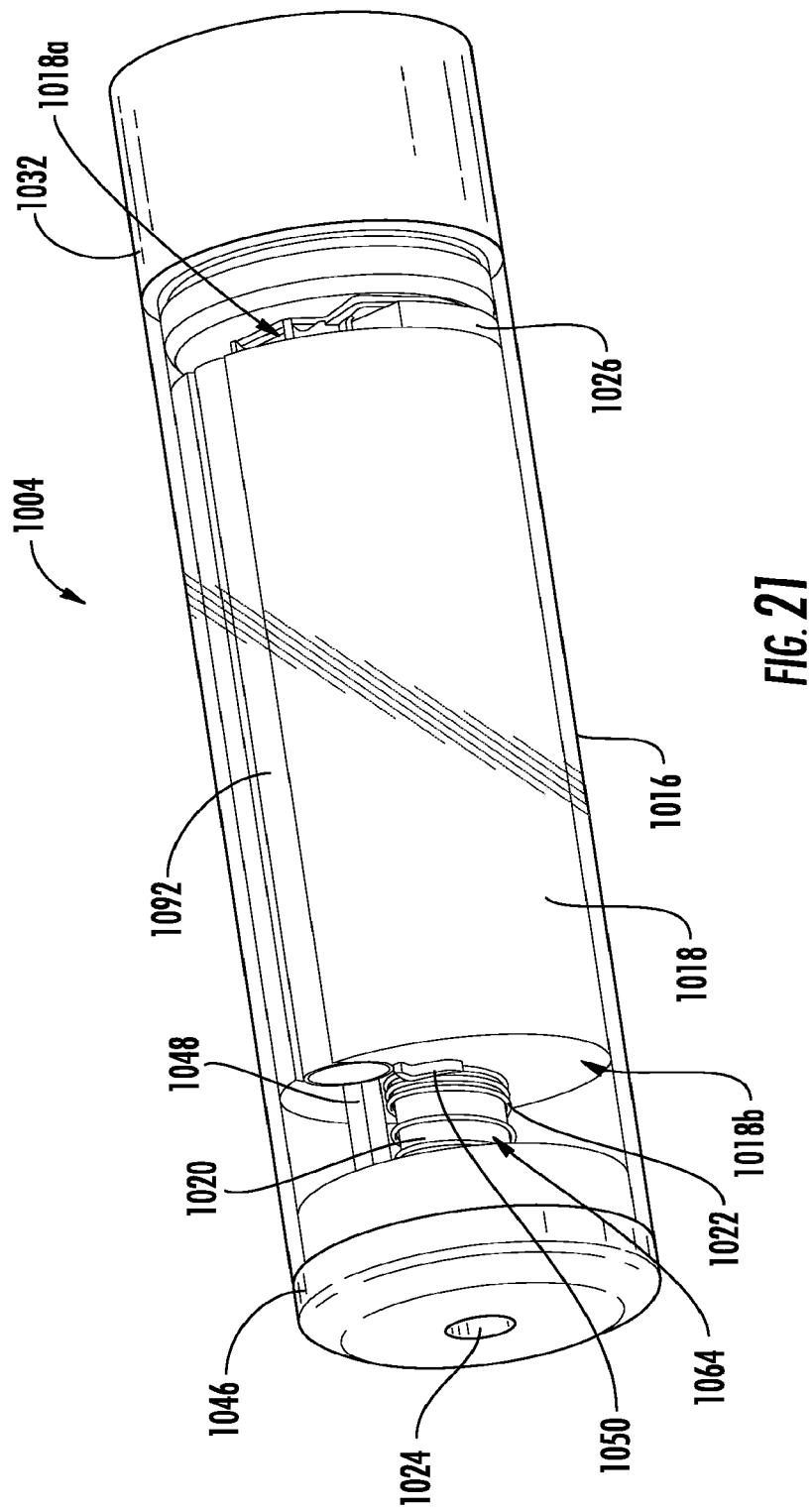
Figure 22:
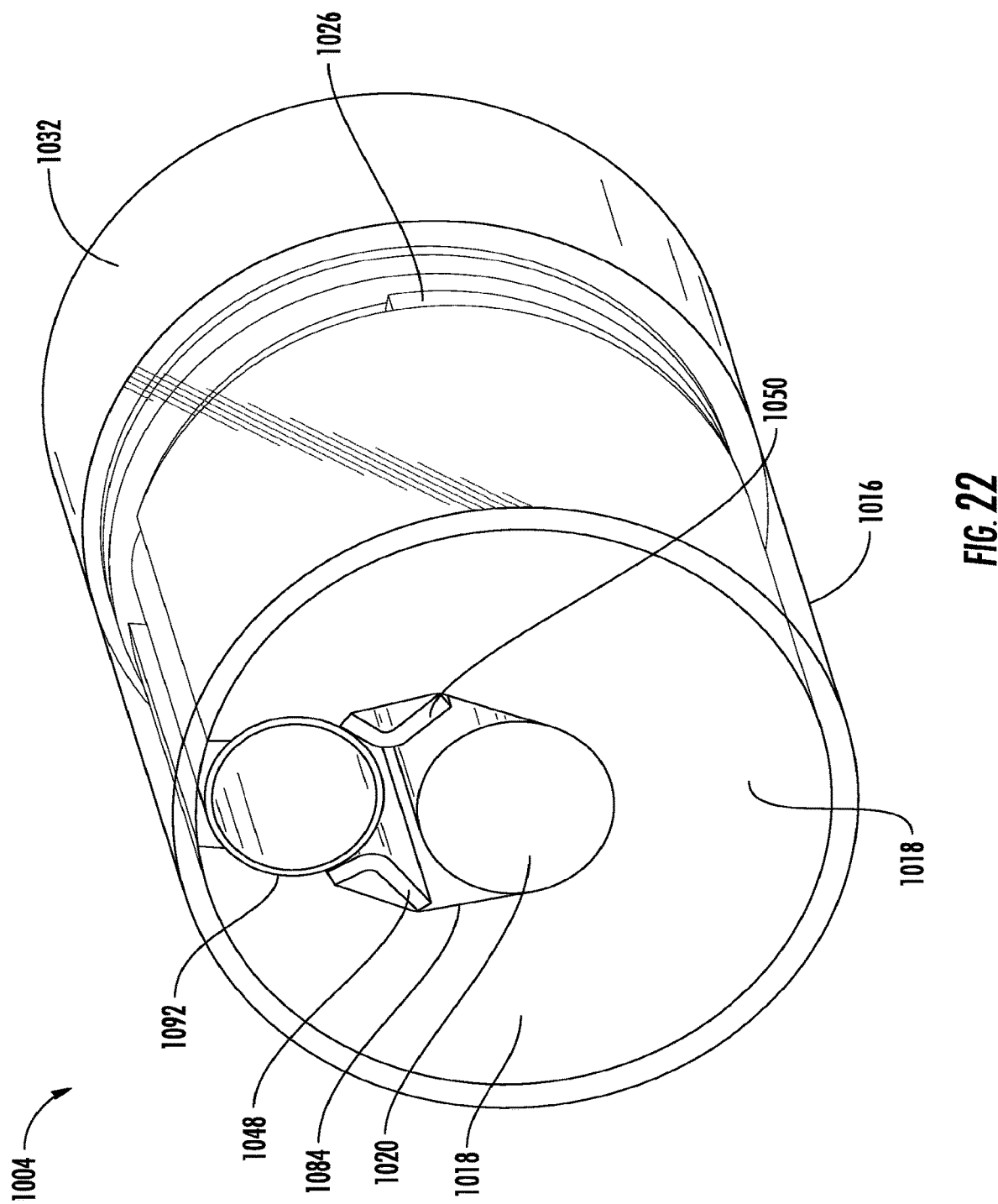

Having thus described the disclosure in the foregoing general terms, reference will now be made to the accompanying drawings, which are not necessarily drawn to scale, and wherein:

FIG. 1 illustrates a longitudinal sectional view through an aerosol delivery device comprising a control body and a cartridge including a reservoir and a liquid transport element according to an example embodiment of the present disclosure;

FIG. 2 illustrates a longitudinal cross-section through a perspective view of a cartridge for an aerosol delivery device comprising a unitary reservoir and liquid transport element surrounding a heating element according to an example embodiment of the present disclosure;

FIG. 3 illustrates a lateral cross-section through a perspective view of the unitary reservoir and liquid transport element of FIG. 2 according to an example embodiment of the present disclosure;

FIG. 4 illustrates a modified perspective view of a cartridge for an aerosol delivery device comprising a unitary reservoir and liquid transport element including a protrusion proximate a mouthpiece and about which a heating element extends according to an example embodiment of the present disclosure;

FIG. 5 illustrates a perspective view of the unitary reservoir and liquid transfer element of FIG. 4 according to an example embodiment of the present disclosure;

FIG. 6 illustrates a modified perspective view of a cartridge for an aerosol delivery device comprising a unitary reservoir and liquid transport element including a protrusion proximate a base and about which a heating element extends according to an example embodiment of the present disclosure;

FIG. 7 illustrates a modified lateral cross-section through a perspective view of the cartridge of FIG. 6 according to an example embodiment of the present disclosure;

FIG. 8 illustrates a partial end view of the unitary reservoir and liquid transport element of FIG. 6 according to an example embodiment of the present disclosure;

FIG. 9 illustrates a perspective view of terminals, an electronic component, and a base of the cartridge of FIG. 6 according to an example embodiment of the present disclosure;

FIG. 10 illustrates a modified perspective view of a cartridge for an aerosol delivery device comprising a unitary reservoir and liquid transport element and a laterally-extending electronic component according to an example embodiment of the present disclosure;

FIG. 11 illustrates a perspective view of the unitary reservoir and liquid transport element of the cartridge of FIG. 10 according to an example embodiment of the present disclosure;

FIG. 12 illustrates a perspective view of terminals, an electronic component, and a base of the cartridge of FIG. 10 according to an example embodiment of the present disclosure;

FIG. 13 schematically illustrates a method for producing a vapor according to an example embodiment of the present disclosure;

FIG. 14 illustrates a longitudinal cross-section through a perspective view of a cartridge for an aerosol delivery device including a heating element and an electronic component received in a liquid transport element, the liquid transport element being received in a reservoir according to an example embodiment of the present disclosure;

FIG. 15 illustrates a perspective view of the liquid transport element of FIG. 14;

FIG. 16 illustrates a modified perspective view of a cartridge for an aerosol delivery device including a liquid transport element defining a protrusion at which a heating element is positioned, the liquid transport element being received in a reservoir according to an example embodiment of the present disclosure;

FIG. 17 illustrates a lateral cross-section through a perspective view of the cartridge of FIG. 16;

FIG. 18 illustrates a perspective view of the liquid transport element and an electronic component of the cartridge of FIG. 16 according to an example embodiment of the present disclosure;

FIG. 19 illustrates a modified longitudinal cross-section through a perspective view of a cartridge for an aerosol delivery device including a liquid transport element defining a protrusion at which a heating element is positioned, the liquid transport element being received in a reservoir, and a laterally-extending electronic component according to an example embodiment of the present disclosure;

FIG. 20 illustrates a lateral cross-section through a perspective view of the cartridge of FIG. 19;

FIG. 21 illustrates a modified perspective view of a cartridge for an aerosol delivery device including a liquid transport element defining a protrusion at which a heating element is positioned, the liquid transport element and a flow director being received in a reservoir, and a laterally-extending electronic component according to an example embodiment of the present disclosure;

FIG. 22 illustrates a lateral cross-section through a perspective view of the cartridge of FIG. 21; and FIG. 23 schematically illustrates a method for producing an aerosol delivery device according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke—i.e., from by-products of combustion or pyrolysis of tobacco, but rather, use of those preferred systems results in the production of vapors/aerosols resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like. The devices described herein, however, are not limited to devices that are substantially shaped and dimensioned as a traditional cigarette. Rather, the present devices may take on any shape and can be substantially larger than a traditional cigarette.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. In exemplary embodiments, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one embodiment, all of the components of the aerosol delivery device are contained within one housing. Alternatively, an aerosol delivery device can comprise two or more housings that are joined and are separable. For example, an aerosol delivery device can possess at one end a control body comprising a housing containing one or more components (e.g., a battery and/or capacitor and various electronics for controlling the operation of that article), and at the other end and removably attached thereto an outer body or shell containing aerosol forming components (e.g., one or more aerosol precursor components, such as flavors and aerosol formers, one or more heating elements, and/or one or more wicks).

Aerosol delivery devices of the present disclosure can include an outer housing or shell that is not substantially tubular in shape but may be formed to substantially greater dimensions—i.e., be substantially "palm-sized" for being held in the palm of a user. The housing or shell can be configured to include a mouthpiece and/or may be configured to receive a separate shell (e.g., a cartridge) that can include consumable elements, such as an aerosol precursor composition, and can include a vaporizer or atomizer.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), a heating element or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

One example embodiment of an aerosol delivery device 100 illustrating components that may be utilized in an aerosol delivery device according to the present disclosure is provided in FIG. 1. As seen in the sectional view illustrated therein, the aerosol delivery device 100 can include a control body 102 and a cartridge 104 that can be permanently or detachably aligned in a functioning relationship. The control body 102 and the cartridge 104 can be engaged via press fit (as illustrated), threaded engagement, interference fit, magnetic attraction, or the like. In particular, connection components, such as those further described herein may be used. For example, the control body may include a coupler that is adapted to engage a connector on the cartridge.

In specific embodiments, one or both of the control body 102 and the cartridge 104 may be referred to as being disposable or as being reusable. For example, the control body may have a replaceable battery or a rechargeable battery and thus may be unitary with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. Pat. Pub. No. 2014/0261495 to Novak et al., which is incorporated herein by reference in its entirety. Further, in some embodiments the cartridge may comprise a single-use cartridge, as disclosed in U.S. Pat. No. 8,910,639 to Chang et al., which is incorporated herein by reference in its entirety.

As illustrated in FIG. 1, the control body 102 can comprise an outer body 106. A control component 108 (e.g., a printed circuit board (PCB), an integrated circuit, a memory component, a microcontroller, or the like), a flow sensor 110 (e.g., a pressure sensor), a battery 112, and a light emitting diode (LED) 114 may be positioned within the outer body 106 in any of various alignments. Further indicators (e.g., a haptic feedback component, an audio feedback component, or the like) can be included in addition to or as an alternative to the LED 114. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. Pat. App. Pub. No. 2015/0216233, to Sears et al.; which are incorporated herein by reference.

The cartridge 104 can include an outer body 116. The outer body 116 may enclose a reservoir 118 that is in fluid communication with a liquid transport element 120 adapted to wick or otherwise transport an aerosol precursor composition stored in the reservoir housing to a heating element 122. Various embodiments of materials configured to produce heat when electrical current is applied therethrough may be employed to form the resistive heating element 122. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, graphite and graphite-based materials (e.g., carbon-based foams and yarns) and ceramics (e.g., positive or negative temperature coefficient ceramics). As further described herein, a heating element may comprise a variety of materials configured to provide electromagnetic radiation, including laser diodes.

A mouth opening 124 may be present in the outer body 116 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include an electronic component 126, which may include an integrated circuit, a memory component, a sensor, or the like. The electronic component 126 of the cartridge 104 may be adapted to communicate with the control component 108 of the control body 102 and/or with an external device by wired or wireless means. The electronic component 126 may be positioned anywhere within the cartridge 104.

Although the control component 108 and the flow sensor 110 are illustrated separately, it should be understood that the control component and the flow sensor may be unitary as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some embodiments, the air flow sensor may comprise its own circuit board or other base element to which it can be attached. In some embodiments, a flexible circuit board may be utilized. A flexible circuit board may be configured into a variety of shapes, including substantially tubular shapes.

The control body 102 and the cartridge 104 may include components adapted to facilitate a fluid engagement therebetween. As illustrated in FIG. 1, the control body 102 can include a coupler 128 having a cavity 130 defined therein. The cartridge 104 can include a base 132 adapted to engage the coupler 128 and can include a projection 134 adapted to fit within the cavity 130 defined by the coupler 128. Such engagement can facilitate a stable connection between the control body 102 and the cartridge 104 as well as establish an electrical connection between the battery 112 and control component 108 in the control body and the heating element 122 and the electronic component 126 in the cartridge. Further, the outer body 106 can include an air intake 136, which may be a notch in the shell where it connects to the coupler 128 that allows for passage of ambient air around the coupler and into the shell where it then passes through the cavity 130 of the coupler and into the cartridge 104 through the projection 134.

A coupler and a base useful according to the present disclosure are described in U.S. Pat. Pub. No. 2014/0261495 to Novak et al., the disclosure of which is incorporated herein by reference in its entirety. For example, the coupler 128 as seen in FIG. 1 may define an outer periphery 138 configured to mate with an inner periphery 140 of the base 132. In one embodiment the inner periphery of the base may define a radius that is substantially equal to, or slightly greater than, a radius of the outer periphery of the coupler. Further, the coupler 128 may define one or more protrusions 142 at the outer periphery 138 configured to engage one or more recesses 144 defined at the inner periphery of the base. However, various other embodiments of structures, shapes, and components may be employed to couple the base to the coupler. In some embodiments the connection between the base 132 of the cartridge 104 and the coupler 128 of the control body 102 may be substantially permanent, whereas in other embodiments the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some embodiments. In other embodiments, further shapes and dimensions are encompassed—e.g., a rectangular or triangular cross-section, multifaceted shapes, fob shaped, or the like.

The reservoir 118 illustrated in FIG. 1 can take on any design configured for retaining a liquid, such as a container or a mass configured for absorbing and/or adsorbing the liquid—e.g., a fibrous reservoir is often employed in existing embodiments of reservoirs. Or, as described hereinafter, the reservoir 118 may comprise a porous monolith. As illustrated in FIG. 1, the reservoir 118 can comprise one or more layers of nonwoven fibers substantially formed into the shape of a tube encircling the interior of the outer body 116. An aerosol precursor composition can be retained in the reservoir 118.

The reservoir 118 can be in fluid connection with a liquid transport element 120. The liquid transport element 120 can transport the aerosol precursor composition stored in the reservoir 118 via capillary action to the heating element 122 that is in the form of a metal wire coil in this embodiment. As such, the heating element 122 is in a heating arrangement with the liquid transport element 120. In some embodiments of existing aerosol delivery devices, the liquid transport element comprises fiberglass or other fibrous material. However, as described hereinafter, in other embodiments the liquid transport element may comprise a porous monolith.

In use, when a user draws on the article 100, airflow is detected by the sensor 110, the heating element 122 is activated, and the components for the aerosol precursor composition are vaporized by the heating element 122. Drawing upon the mouthend of the article 100 causes ambient air to enter the air intake 136 and pass through the cavity 130 in the coupler 128 and the central opening in the projection 134 of the base 132 of the cartridge 104. In the cartridge 104, the drawn air combines with the formed vapor to form an aerosol. The aerosol is whisked, aspirated, or otherwise drawn away from the heating element 122 and out the mouth opening 124 in the mouthend of the article 100.

An input device (e.g., a user interface) may be included with the aerosol delivery device. The input may be included to allow a user to control functions of the device and/or for output of information to a user. Any component or combination of components may be utilized as an input for controlling the function of the device. For example, one or more pushbuttons may be used as described in U.S. Pat. App. Pub. No. 2015/0245658, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See, for example, U.S. Pat. App. Pub. No. 2016/0158782, to Henry et al., which is incorporated herein by reference.

In some embodiments, an input may comprise a computer or computing device, such as a smartphone or tablet. In particular, the aerosol delivery device may be wired to the computer or other device, such as via use of a USB connector or similar protocol. The aerosol delivery device also may communicate with a computer or other device acting as an input via wireless communication. See, for example, the systems and methods for controlling a device via a read request as described in U.S. Pat. App. Pub. No. 2016/0007651, to Ampolini et al., the disclosure of which is incorporated herein by reference. In such embodiments, an application or other computer program may be used in connection with a computer or other computing device to input control instructions to the aerosol delivery device, such control instructions including, for example, the ability to form an aerosol of specific composition by choosing the nicotine content and/or content of further flavors to be included.

The various components of an aerosol delivery device according to the present disclosure can be chosen from components described in the art and commercially available. Representative commercially-available products include AVIGO, VUSE, VUSE CONNECT, VUSE FOB and VUSE HYBRID by R. J. Reynolds Vapor Company. Examples of batteries that can be used according to the disclosure are described in U.S. Pat. Pub. No. 2010/0028766 to Peckerar et al., the disclosure of which is incorporated herein by reference in its entirety.

As noted above, the aerosol delivery device can incorporate a sensor or detector (e.g., the flow sensor 110) for control of supply of electric power to the heating element 122 when aerosol generation is desired (e.g., upon draw during use). As such, for example, there is provided a manner or method for turning off the power supply to the heat generation element when the aerosol delivery device is not be drawn upon during use, and for turning on the power supply to actuate or trigger the generation of heat by the heat generation element during draw. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference.

The aerosol delivery device most preferably incorporates a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. Pub. Nos. 2009/0230117 to Fernando et al., 2014/0060554 to Collett et al., and 2014/0270727 to Ampolini et al.; and U.S. Pat. App. Pub. No. 2015/0257445, to Henry et al.; which are incorporated herein by reference.

Representative types of substrates, reservoirs or other components for supporting the aerosol precursor are described in U.S. Pat. No. 8,528,569 to Newton; U.S. Pat. Pub. Nos. 2014/0261487 to Chapman et al., 2014/0059780 to Davis et al. and 2015/0216232 to Bless et al.; which are incorporated herein by reference. Additionally, various wicking materials, and the configuration and operation of those wicking materials within certain types of electronic cigarettes, are set forth in U.S. Pat. No. 8,910,640 to Sears et al.; which is incorporated herein by reference.

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Most preferably, the aerosol precursor composition is comprised of a combination or mixture of various ingredients or components. The selection of the particular aerosol precursor components, and the relative amounts of those components used, may be altered in order to control the overall chemical composition of the mainstream aerosol produced by the aerosol generation arrangement(s). Of particular interest are aerosol precursor compositions that can be characterized as being generally liquid in nature. For example, representative generally liquid aerosol precursor compositions may have the form of liquid solutions, viscous gels, mixtures of miscible components, or liquids incorporating suspended or dispersed components. Typical aerosol precursor compositions are capable of being vaporized upon exposure to heat under those conditions that are experienced during use of the aerosol generation arrangement(s) that are characteristic of the present disclosure; and hence are capable of yielding vapors and aerosols that are capable of being inhaled.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract (e.g., an extract from which the nicotine is derived), such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

As noted above, highly purified tobacco-derived nicotine (e.g., pharmaceutical grade nicotine having a purity of greater than 98% or greater than 99%) or a derivative thereof can be used in the devices of the present disclosure. Representative nicotine-containing extracts can be provided using the techniques set forth in U.S. Pat. No. 5,159,942 to Brinkley et al., which is incorporated herein by reference. In certain embodiments, the products of the present disclosure can include nicotine in any form from any source, whether tobacco-derived or synthetically-derived. Nicotinic compounds used in the products of the present disclosure can include nicotine in free base form, salt form, as a complex, or as a solvate. See, for example, the discussion of nicotine in free base form in U.S. Pat. Pub. No. 2004/0191322 to Hansson, which is incorporated herein by reference. At least a portion of the nicotinic compound can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, Beitrage Tabakforschung Int., 12, 43-54 (1983). Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate), chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotinic compound is in the form of a salt with an organic acid moiety, including, but not limited to, levulinic acid as discussed in U.S. Pat. Pub. No. 2011/0268809 to Brinkley et al., which are incorporated herein by reference.

The aerosol precursor composition may also incorporate so-called "aerosol forming materials." Such materials may, in some instances, have the ability to yield visible (or not visible) aerosols when vaporized upon exposure to heat under those conditions experienced during normal use of aerosol generation arrangement(s) that are characteristic of the present disclosure. Such aerosol forming materials include various polyols or polyhydric alcohols (e.g., glycerin, propylene glycol, and mixtures thereof). Aspects of the present disclosure also incorporate aerosol precursor components that can be characterized as water, saline, moisture or aqueous liquid. During conditions of normal use of certain aerosol generation arrangement(s), the water incorporated within those aerosol generation arrangement(s) can vaporize to yield a component of the generated aerosol. As such, for purposes of the current disclosure, water that is present within the aerosol precursor composition may be considered to be an aerosol forming material.

It is possible to employ a wide variety of optional flavoring agents or materials that alter the sensory character or nature of the drawn mainstream aerosol generated by the aerosol delivery system of the present disclosure. For example, such optional flavoring agents may be used within the aerosol precursor composition or substance to alter the flavor, aroma and organoleptic properties of the aerosol. Certain flavoring agents may be provided from sources other than tobacco. Exemplary flavoring agents may be natural or artificial in nature, and may be employed as concentrates or flavor packages.

Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar and pipe tobaccos. Syrups, such as high fructose corn syrup, also can be employed. Certain flavoring agents may be incorporated within aerosol forming materials prior to formulation of a final aerosol precursor mixture (e.g., certain water soluble flavoring agents can be incorporated within water, menthol can be incorporated within propylene glycol, and certain complex flavor packages can be incorporated within propylene glycol). However, in some aspects of the present disclosure, the aerosol precursor composition is free of any flavorants, flavor characteristics or additives.

Aerosol precursor compositions also may include ingredients that exhibit acidic or basic characteristics (e.g., organic acids, ammonium salts or organic amines). For example, certain organic acids (e.g., levulinic acid, succinic acid, lactic acid, and pyruvic acid) may be included in an aerosol precursor formulation incorporating nicotine, preferably in amounts up to being equimolar (based on total organic acid content) with the nicotine. For example, the aerosol precursor may include about 0.1 to about 0.5 moles of levulinic acid per one mole of nicotine, about 0.1 to about 0.5 moles of succinic acid per one mole of nicotine, about 0.1 to about 0.5 moles of lactic acid per one mole of nicotine, about 0.1 to about 0.5 moles of pyruvic acid per one mole of nicotine, or various permutations and combinations thereof, up to a concentration wherein the total amount of organic acid present is equimolar to the total amount of nicotine present in the aerosol precursor composition. However, in some aspects of the present disclosure, the aerosol precursor composition is free of any acidic (or basic) characteristics or additives.

As one non-limiting example, a representative aerosol precursor composition or substance can include glycerin, propylene glycol, water, saline, and nicotine, and combinations or mixtures of any or all of those components. For example, in one instance, a representative aerosol precursor composition may include (on a weight basis) about 70% to about 100% glycerin, and often about 80% to about 90% glycerin; about 5% to about 25% water, often about 10% to about 20% water; and about 0.1% to about 5% nicotine, often about 2% to about 3% nicotine. In one particular non-limiting example, a representative aerosol precursor composition may include about 84% glycerin, about 14% water, and about 2% nicotine. The representative aerosol precursor composition may also include propylene glycol, optional flavoring agents or other additives in varying amounts on a weight basis. In some instances, the aerosol precursor composition may comprise up to about 100% by weight of any of glycerin, water, and saline, as necessary or desired.

Representative types of aerosol precursor components and formulations also are set forth and characterized in U.S. Pat. No. 7,217,320 to Robinson et al.; U.S. Pat. No. 8,881, 737 to Collett et al. and U.S. Pat. No. 9,254,002 to Chong et al.; and U.S. Pat. Pub. Nos. 2013/0008457 to Zheng et al.; 2015/0020823 to Lipowicz et al. and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Yet other features, controls or components that can be incorporated into aerosol delivery systems of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. No. 8,689,804 to Fernando et al. and U.S. Pat. No. 9,220,302 to DePiano et al.; U.S. Pat. Pub. Nos. 2013/0192623 to Tucker et al.; 2013/0298905 to Leven et al.; 2013/0180553 to Kim et al., 2014/0000638 to Sebastian et al. and 2014/0261495 to Novak et al., which are incorporated herein by reference.

The foregoing description of use of the article can be applied to the various embodiments described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article illustrated in FIG. 1 or as otherwise described above may be included in an aerosol delivery device according to the present disclosure.

In one or more embodiments, the present disclosure can relate to the use of a porous monolithic material in one or more components of an aerosol delivery device. As used herein, a "porous monolithic material" or "porous monolith" is intended to mean comprising a substantially single unit which, in some embodiments, may be a single piece formed, composed, or created without joints or seams and comprising a substantially, but not necessarily rigid, uniform whole. In some embodiments, a monolith according to the present disclosure may be undifferentiated, i.e., formed of a single material, or may be formed of a plurality of units that are permanently combined, such as a sintered conglomerate. Thus, in some embodiments the porous monolith may comprise an integral porous monolith.

In some embodiments, the use of a porous monolith particularly can relate to the use of a porous glass in components of an aerosol delivery device. As used herein, "porous glass" is intended to refer to glass that has a three-dimensional interconnected porous microstructure. The term specifically can exclude materials made of bundles (i.e., wovens or non-wovens) of glass fibers. Thus, porous glass can exclude fibrous glass. Porous glass may also be referred to as controlled pore glass (CPG) and may be known by the trade name VYCOR®. Porous glass suitable for use according to the present disclosure can be prepared by known methods such as, for example, metastable phase separation in borosilicate glasses followed by liquid extraction (e.g., acidic extraction or combined acidic and alkaline extraction) of one of the formed phases, via a sol-gel process, or by sintering of glass powder. The porous glass particularly can be a high-silica glass, such as comprising 90% or greater, 95%, 96% or greater, or 98% or greater silica by weight. Porous glass materials and methods of preparing porous glass that can be suitable for use according to the present disclosure are described in U.S. Pat. No. 2,106,744 to Hood et al., U.S. Pat. No. 2,215,039 to Hood et al., U.S. Pat. No. 3,485,687 to Chapman et al., U.S. Pat. No. 4,657,875 to Nakashima et al., U.S. Pat. No. 9,003,833 to Kotani et al., U.S. Pat. Pub. No. 2013/0045853 to Kotani et al., U.S. Pat. Pub. No. 2013/0067957 to Zhang et al., U.S. Pat. Pub. No. 2013/0068725 to Takashima et al., and U.S. Pat. Pub. No. 2014/0075993 to Himanshu, the disclosures of which are incorporated herein by reference. Although the term porous "glass" may be used herein, it should not be construed as limiting the scope of the disclosure in that a "glass" can encompass a variety of silica based materials.

The porous glass can be defined in some embodiments in relation to its average pore size. For example, the porous glass can have an average pore size of about 1 nm to about 1000 µm, about 2 nm to about 500 µm, about 5 nm to about 200 µm, or about 10 nm to about 100 µm. In certain embodiments, porous glass for use according to the present disclosure can be differentiated based upon the average pore size. For example, a small pore porous glass can have an average pore size of 1 nm up to 500 nm, an intermediate pore porous class can have an average pore size of 500 nm up to 10 µm, and a large pore porous glass can have an average pore size of 10 µm up to 1000 µm. In some embodiments, a large pore porous glass can preferably be useful as a storage element, and a small pore porous glass and/or an intermediate pore porous glass can preferably be useful as a transport element.

The porous glass also can be defined in some embodiments in relation to its surface area. For example, the porous glass can have a surface area of at least 100 m$^2$/g, at least 150 m$^2$/g, at least 200 m$^2$/g, or at least 250 m$^2$/g, such as about 100 m$^2$/g to about 600 m$^2$/g, about 150 m$^2$/g to about 500 m$^2$/g, or about 200 m$^2$/g to about 450 m$^2$/g.

The porous glass can be defined in some embodiments in relation to its porosity (i.e., the volumetric fraction of the material defining the pores). For example, the porous glass can have a porosity of at least 20%, at least 25%, or at least 30%, such as about 20% to about 80%, about 25% to about 70%, or about 30% to about 60% by volume. In certain embodiments, a lower porosity may be desirable, such as a porosity of about 5% to about 50%, about 10% to about 40%, or about 15% to about 30% by volume.

The porous glass can be further defined in some embodiments in relation to its density. For example, the porous glass can have a density of 0.25 g/cm$^3$ to about 3 g/cm$^3$, about 0.5 g/cm$^3$ to about 2.5 g/cm$^3$, or about 0.75 g/cm$^3$ to about 2 g/cm$^3$.

In some embodiments, the use of a porous monolith particularly can relate to the use of a porous ceramic in components of an aerosol delivery device. As used herein, "porous ceramic" is intended to refer to a ceramic material that has a three-dimensional interconnected porous microstructure. Porous ceramic materials and methods of making porous ceramics suitable for use according to the present disclosure are described in U.S. Pat. No. 3,090,094 to Schwartzwalder et al., U.S. Pat. No. 3,833,386 to Frisch et al., U.S. Pat. No. 4,814,300 to Helferich, U.S. Pat. No. 5,171,720 to Kawakami, U.S. Pat. No. 5,185,110 to Kunikazu et al., U.S. Pat. No. 5,227,342 to Anderson et al., U.S. Pat. No. 5,645,891 to Liu et al., U.S. Pat. No. 5,750,449 to Niihara et al., U.S. Pat. No. 6,753,282 to Fleischmann et al., U.S. Pat. No. 7,208,108 to Otsuka et al., U.S. Pat. No. 7,537,716 to Matsunaga et al., U.S. Pat. No. 8,609,235 to Hotta et al., the disclosures of which are incorporated herein by reference. Although the term porous "ceramic" may be used herein, it should not be construed as limiting the scope of the disclosure in that a "ceramic" can encompass a variety of alumina based materials.

The porous ceramic likewise can be defined in some embodiments in relation to its average pore size. For example, the porous ceramic can have an average pore size of about 1 nm to about 1000 μm, about 2 nm to about 500 μm, about 5 nm to about 200 μm, or about 10 nm to about 100 μm. In certain embodiments, porous ceramic for use according to the present disclosure can be differentiated based upon the average pore size. For example, a small pore porous ceramic can have an average pore size of 1 nm up to 500 nm, an intermediate pore porous ceramic can have an average pore size of 500 nm up to 10 μm, and a large pore porous ceramic can have an average pore size of 10 μm up to 1000 μm. In some embodiments, a large pore porous ceramic can preferably be useful as a storage element, and a small pore porous ceramic and/or an intermediate pore porous ceramic can preferably be useful as a transport element.

The porous ceramic also can be defined in some embodiments in relation to its surface area. For example, the porous ceramic can have a surface area of at least 100 $m^2/g$, at least 150 $m^2/g$, at least 200 $m^2/g$, or at least 250 $m^2/g$, such as about 100 $m^2/g$ to about 600 $m^2/g$, about 150 $m^2/g$ to about 500 $m^2/g$, or about 200 $m^2/g$ to about 450 $m^2/g$.

The porous ceramic can be defined in some embodiments in relation to its porosity (i.e., the volumetric fraction of the material defining the pores). For example, the porous ceramic can have a porosity of at least 20%, at least 25%, or at least 30%, such as about 20% to about 80%, about 25% to about 70%, or about 30% to about 60% by volume. In certain embodiments, a lower porosity may be desirable, such as a porosity of about 5% to about 50%, about 10% to about 40%, or about 15% to about 30% by volume.

The porous ceramic can be further defined in some embodiments in relation to its density. For example, the porous ceramic can have a density of 0.25 $g/cm^3$ to about 3 $g/cm^3$, about 0.5 $g/cm^3$ to about 2.5 $g/cm^3$, or about 0.75 $g/cm^3$ to about 2 $g/cm^3$.

Although silica-based materials (e.g., porous glass) and alumina-based materials (e.g., porous ceramic) may be discussed separately herein, it is understood that a porous monolith, in some embodiments, can comprise a variety of aluminosilicate materials. For example, various zeolites may be utilized according to the present disclosure. Thus, by way of example, the porous monoliths discussed herein may comprise one or both of a porous glass and a porous ceramic, which may be provided as a composite. In one embodiment such a composite may comprise $SiO_2$ and $Al_2O_3$.

A porous monolith used according to the present disclosure can be provided in a variety of sizes and shapes. Preferably, the porous monolith may be substantially elongated, substantially flattened or planar, substantially curved (e.g., "U-shaped"), substantially in the form of a walled cylinder, or in any other form suitable for use according to the present disclosure. Additional example shapes of the porous monolith are described hereinafter and illustrated in the figures.

In one or more embodiments, a porous monolith according to the present disclosure can be characterized in relation to wicking rate. As a non-limiting example, wicking rate can be calculated by measuring the mass uptake of a known liquid, and the rate (in mg/s) can be measured using a microbalance tensiometer or similar instrument. Preferably, the wicking rate is substantially within the range of the desired mass of aerosol to be produced over the duration of a puff on an aerosol forming article including the porous monolith. Wicking rate can be, for example, in the range of about 0.05 mg/s to about 15 mg/s, about 0.1 mg/s to about 12 mg/s, or about 0.5 mg/s to about 10 mg/s. Wicking rate can vary based upon the liquid being wicked. In some embodiments, wicking rates as described herein can be referenced to substantially pure water, substantially pure glycerol, substantially pure propylene glycol, a mixture of water and glycerol, a mixture of water and propylene glycol, a mixture of glycerol and propylene glycol, or a mixture of water, glycerol, and propylene glycol. Wicking rate also can vary based upon the use of the porous monolith. For example, a porous monolith used as a liquid transport element may have a greater wicking rate than a porous monolith used as a reservoir. Wicking rates may be varied by control of one or more of pore size, pore size distribution, and wettability, as well as the composition of the material being wicked.

As noted above, some existing embodiments of aerosol delivery devices comprise a liquid transport element and/or a reservoir comprising a fibrous material. However, fibrous materials may suffer from certain detriments. In this regard, in view of the heating element being positioned in proximity to the liquid transport element, scorching could occur at the fibrous liquid transport element which could detrimentally affect the flavor of the aerosol produced and/or the structural integrity of the liquid transport element. Depending on the relative position of the components, scorching could also occur at the fibrous reservoir.

Further, fibrous materials may in general be relatively weak and prone to tearing or other failure when subjected to stresses such as may occur during repeated drop events or other severe incidents. Additionally, usage of fibrous materials in the air flow path may present challenges during assembly in terms of ensuring that no loose fibers are present. Due to the flexible nature of fibrous materials, it may also be difficult to form, and retain, the liquid transport element and the reservoir in desired shapes.

Accordingly, aerosol delivery devices of the present disclosure may include a reservoir and/or liquid transport element comprising a porous monolith. As may be understood, usage of a porous monolith may not suffer from the above-noted potential detriments. In this regard, a relatively more durable material such as a porous glass or porous ceramic may be selected, which may not tear. Further, such a material may not be subject to scorching. Additionally, the absence of fibers in porous monoliths eliminates issues with respect movement of fibers in the airflow path defined therethrough. Further, porous monoliths may be formed in substantially any shape and may be shape stable.

By way of example, FIG. 2 illustrates a modified sectional view through a cartridge 204 for an aerosol delivery device.

The cartridge 204 may include some or all of the components of the cartridge 104 (see, FIG. 1) described above. Further, the cartridge 204 may be useable with the control body 102 described above and/or other embodiments of control bodies.

As illustrated, the cartridge 204 may include an outer body 216 and a base 232 coupled to one end of the outer body. A mouth opening 224 may be positioned at an opposing end of the outer body 216. An electronic component 226 and a heating element 222 may be positioned within the outer body 216.

The mouth opening 224 may be defined in a mouthpiece 246, which may be engaged with an end of the outer body 216 opposite from the base 232. A first heating terminal 248 and a second heating terminal 250 may be coupled to the heating element 222. Further, an electronic component terminal 252 may engage the electronic component 226. The first and second heating terminals 248, 250 may also engage the electronic component 226. The terminals 248, 250, 252 may extend into the base 232 to allow for electrical connectivity with a control body as described above.

Additionally, the cartridge 204 may include a unitary reservoir and liquid transport element 254. The term "unitary," as used herein with respect to the context of the unitary reservoir and liquid transport element 254, refers to the reservoir and liquid transport element being a formed continuous piece, with a seamless transition from the reservoir to the liquid transport element. In this regard, the unitary reservoir and liquid transport element 254 may comprise a porous monolith such as a porous glass or porous ceramic as described above, which may be integral.

The unitary reservoir and liquid transport element 254 may contain an aerosol precursor composition. The unitary reservoir and liquid transport element 254 may be positioned proximate the heating element 222. Thereby, the heating element 222 may heat the aerosol precursor composition contained by the unitary reservoir and liquid transport element 254 to produce vapor.

FIG. 3 illustrates a sectional view through the unitary reservoir and liquid transport element 254. As illustrated, in some embodiments the unitary reservoir and liquid transport element 254 may define at least one channel 255 extending at least partially therethrough. The heating element 222 may be positioned in a first section 256 of the channel 255. Thereby, the heating element 222 may be substantially surrounded by, and in contact with, the unitary reservoir and liquid transport element 254 so as to heat the aerosol precursor composition contained therein to produce vapor. In some embodiments the first heating terminal 248 and/or the second heating terminal 250 may extend into the first section 256 of the channel 255 to engage opposing ends of the heating element 222. As illustrated, the heating element 222 may comprise a coiled wire.

As illustrated in FIG. 3, the channel 255 extending at least partially through the unitary reservoir and liquid transport element 254 may further define a second section 258. As illustrated in FIG. 2, the electronic component 226 may be received in the second section 258 of the channel 255. In this regard, the electronic component 226 may be positioned between the first heating terminal 248 and the second heating terminal 250. Thus, in this embodiment the heating element 222, the heating terminals 248, 250, and the electronic component 226 are at least partially received in the channel 255. As described below, the first section 256 and the second section of the channel 255 may define an airflow channel through the cartridge.

The heating element 222 may define a central longitudinal axis, which may be substantially parallel to a longitudinal axis of the outer body 216. For example, the longitudinal axis of the heating element 222 may be coaxial with a longitudinal axis of the outer body 216. Further, a longitudinal axis of the electronic component 226 may extend substantially parallel to the longitudinal axis of the outer body 226. Further, the channel 255 may extend substantially parallel to the longitudinal axis of the outer body 226. For example, the channel 255 may be coaxial with the longitudinal axis of the outer body 226.

The unitary reservoir and liquid transport element 254 may extend between a base end 260 and a mouthpiece end 262. The second section 258 of the channel 255 may extend from the base end 260 of the unitary reservoir and liquid transport element 254 to the first section 256 of the channel 255. The first section 256 of the channel 255 may extend from the second section 258 of the channel 255 to the mouthpiece end 262 of the unitary reservoir and liquid transport element 254.

Thereby, an airflow path through the cartridge 204 may extend though the unitary reservoir and liquid transport element 254 from the base end 260 to the mouthpiece end 262. More particularly, the airflow path may extend through the base 232, past the electronic component 226 in the second section 258 of the channel 255, past the heating element 222 in the first section 256 of the channel 255, and out through the mouth opening 224 defined in the mouthpiece 246. Accordingly, vapor produced by heating aerosol precursor composition contained in the unitary reservoir and liquid transport element 254 with the heating element 222 may join with air to form an aerosol directed to the user through the mouthpiece 246.

Thereby, the heating element 222 may be positioned proximate the mouthpiece 246. This configuration may lessen the potential for fluid to condense from the vapor produced by the heating element 222 in the cartridge 204 due to the flow path from the heating element to the mouth opening 224 being relatively short. In this regard, any such condensation would reduce the efficiency of aerosol delivered to the user and could result in issues with respect to fluid leakage from the cartridge 204.

Note that in this embodiment the unitary reservoir and liquid transport element 254 may direct there airflow through the cartridge 204. In this regard, the channel 255 may direct the airflow to the heating element 222, which may be substantially surrounded by the unitary reservoir and liquid transport element 254. Accordingly, usage of a separate flow director may not be required, which may reduce part count and material and/or assembly costs of the cartridge.

Further, the unitary reservoir and liquid transport element 254 contains the aerosol precursor composition and directs the aerosol precursor composition to the heating element 222. Accordingly, the unitary reservoir and liquid transport element 254 may be employed in place of the separate reservoir 118 and liquid transport element 120 (see, FIG. 1). In this regard, the porosity of the unitary reservoir and liquid transport element 254 may allow for fluid movement therethrough. Thereby, as the heating element 222 heats the aerosol precursor composition in the unitary reservoir and liquid transport element 254 positioned proximate thereto, the aerosol precursor composition may redistribute within the unitary reservoir and liquid transport element (e.g., via capillary action). Thus, the unitary reservoir and liquid transport element 254 may be replenished with aerosol precursor composition proximate the heating element 222 by aerosol precursor composition from other positions within the unitary reservoir and liquid transport element.

In some embodiments the unitary reservoir and liquid transport element 254 may define a variable porosity. In other words, the porosity of the unitary reservoir and liquid transport element 254 may vary depending upon a location therein. Thereby, the volumetric fraction of the material defining the pores may vary. By way of further example, in some embodiments the number of pores per unit of volume and/or the size of the pores may vary. Note that a variable porosity, as used herein, is distinguishable from inherent variations in porosity at individual points in the volume of the porous monolith, and instead refers to a porosity gradient occurring between zones or regions therein. As discussed below, by varying the porosity of the unitary reservoir and liquid transport element 254, the characteristics of the unitary reservoir and liquid transport element may vary depending on a location therein.

As may be understood, the cartridges including a unitary reservoir and liquid transport element may define other forms. In this regard, FIG. 4 illustrates a cartridge 304 according to an additional example embodiment of the present disclosure. As illustrated, the cartridge 304 may include an outer body 316 and a base 332 coupled to one end of the outer body. A mouth opening 324 may be positioned at an opposing end of the outer body 316. A heating element 322 may be positioned within the outer body 316.

The mouth opening 324 may be defined in a mouthpiece 346, which may be engaged with an end of the outer body 316 opposite from the base 332. A first heating terminal 348 and a second heating terminal 350 may be coupled to the heating element 322. An electronic component 326 (see, FIG. 5) may be positioned between the first heating terminal 348 and the second heating terminal 350 and an electronic component terminal may engage the electronic component as described above and illustrated, for example, in FIG. 2. Further, the terminals may extend into the base 332 to allow for electrical connectivity with a control body as described above.

Additionally, the cartridge 304 may include a unitary reservoir and liquid transport element 354 that contains an aerosol precursor composition. The unitary reservoir and liquid transport element 354 may extend between a base end 360 and a mouthpiece end 362. The unitary reservoir and liquid transport element 354 may comprise a porous monolith such as a porous glass or porous ceramic, and in some embodiments the unitary reservoir and liquid transport element may define a variable porosity.

Thus, the cartridge 304 may be substantially similar to the cartridge 204 of FIG. 2 in a number of respects. Accordingly, for brevity purposes, particular details of the cartridge 304 shared with the cartridge 204 of FIG. 2 will not be repeated. However, the cartridge 304 may differ in one or more respects.

In this regard, as illustrated in FIG. 4, the heating element 322 may extend at least partially about the unitary reservoir and liquid transport element 354 and in contact therewith. More particularly, the unitary reservoir and liquid transport element 354 may define a protrusion 364, which may be located at a distal end of the unitary reservoir and liquid transport element. In this embodiment the protrusion 364 may be positioned at the mouthpiece end 362 of the unitary reservoir and liquid transport element 354. As illustrated in FIG. 4, the heating element 322 may extend at least partially about the protrusion 364.

As illustrated in FIG. 5, the unitary reservoir and liquid transport element 354 may define one or more channels 355 extending at least partially therethrough. The channels 355 may define a slot 366. As schematically illustrated, the electronic component 326 may be received in the slot 366. Further, the channels 355 may define a first groove 368 and a second groove 370. The grooves 368, 370 may extend on each side of the unitary reservoir and liquid transport element 354 between the protrusion 364 and the slot 366.

As illustrated in FIG. 4, the heating terminals 348, 350 may extend through the slot 366 and the grooves 368, 370. Thereby, the heating terminals 348, 350 may engage the ends of the heating element 322. Further, the electronic component 326 (see, FIG. 5) may be received in the slot 366 between the first heating terminal 348 and the second heating terminal 350. Accordingly, the heating terminals 348, 350 and the electronic component 326 may be at least partially received in the channels 355. Additionally, as may be understood, airflow may define a flow path through the base 332, around the unitary reservoir and liquid transport element 354 through the slot 366 and the grooves 368, 370, past the heating element 322 at which vapor is added thereto, and out the mouthpiece 346 through the mouth opening 324. Thus, the airflow may be directed through the channels 355 extending at least partially through the unitary reservoir and liquid transport element 354.

FIG. 6 illustrates a cartridge 404 according to an additional example embodiment of the present disclosure. As illustrated, the cartridge 404 may include an outer body 416 and a base 432 coupled to one end of the outer body. A mouthpiece 446 may be engaged with an end of the outer body 416 opposite from the base 432. The mouthpiece 446 may define a mouth opening as described above.

A heating element 422 may be positioned within the outer body 416. As illustrated in FIG. 7, the cartridge 404 may further comprise a first heating terminal 448 and a second heating terminal 450, which may be coupled to the heating element 422. An electronic component 426 may be positioned between the first heating terminal 448 and the second heating terminal 450 and an electronic component terminal may engage the electronic component as described above and illustrated, for example, in FIG. 2. Further, the terminals may extend into the base 432 to allow for electrical connectivity with a control body as described above.

Additionally, as illustrated in FIG. 6, the cartridge 404 may include a unitary reservoir and liquid transport element 454 that contains an aerosol precursor composition. The unitary reservoir and liquid transport element 454 may extend between a base end 460 and a mouthpiece end 462. The unitary reservoir and liquid transport element 454 may define a protrusion 464 about which the heating element 422 may at least partially extend in contact therewith. The unitary reservoir and liquid transport element 454 may comprise a porous monolith such as a porous glass or porous ceramic, and in some embodiments the unitary reservoir and liquid transport element may define a variable porosity.

Thus, the cartridge 404 may be substantially similar to the cartridge 304 of FIG. 4 in a number of respects. Accordingly, for brevity purposes, particular details of the cartridge 404 shared with the cartridge 304 of FIG. 4 will not be repeated. However, the cartridge 404 may differ in one or more respects.

In this regard, as illustrated in FIG. 6, the protrusion 464 defined by the unitary reservoir and liquid transport element 454 may be positioned at the base end 460 thereof, rather than the mouthpiece end 462. Further, the unitary reservoir and liquid transport element 454 may include one or more channels 455. For example, as illustrated in FIG. 8, the channels 455 may define a compartment 458.

Further, as illustrated in FIG. 8, the channels 455 may define a recess 472. The recess 472 may extend from the base end 460 of the unitary reservoir and liquid transport element 454 to an opening 474 to the compartment 458. Thereby, as illustrated in FIG. 7, the heating terminals 448, 450 and the electronic component 426 may extend through the recess 472 into the compartment 458. Accordingly, the heating terminals 448, 450 and the electronic component 426 may be at least partially received in the channels 455. Usage of the recess 472 at the base end 460 of the unitary reservoir and liquid transport element 454, rather than extending the compartment 458 to the base end, may allow the heating element 422 to engage the heating terminals 448, 450.

Further, as illustrated in FIG. 6, the channels 455 may define a first groove 468 and a second groove 470. The grooves 468, 470 may extend on each side of the unitary reservoir and liquid transport element 454. In particular, the grooves 468, 470 may start at the heating element 422, which is engaged with the protrusion 464 adjacent the recess 472, and terminate at the mouthpiece end 462 of the unitary reservoir and liquid transport element 454. Accordingly, airflow may define a flow path through the base 432, into the recess 472 (see, e.g., FIG. 8), past the heating element 422 at which vapor is added thereto, around the unitary reservoir and liquid transport element 454 through the grooves 468, 470, and out the mouthpiece 446 through the mouth opening. Thus, the airflow may be directed through the channels 455 extending at least partially through the unitary reservoir and liquid transport element 454.

In the embodiments of cartridges 204, 304, 404 described above the electronic component is received between first and second heating terminals. This configuration is illustrated, by way of example, in the assembly shown in FIG. 9 that is included in the cartridge 404 of FIG. 6. As illustrated, the heating terminals 448, 450 may support the electronic component 426 therebetween.

In this regard, as illustrated, the heating terminals 448, 450 may each define a lateral support section 476 positioned at opposing sides of the electronic component 426. The lateral support sections 476 may restrain lateral movement of the electronic component 426 in lateral directions extending between the first heating terminal 448 and the second heating terminal 450. Further, the heating terminals 448, 450 may each define a primary surface support section 478 that may engage a rear primary surface 426A of the electronic component 426.

The electronic component terminal 452 may engage a front primary surface 426B of the electronic component 426. Additionally, in some embodiments the first heating terminal 448 may include a tab 480 that supplies power to, and engages the front primary surface 426B of the electronic component 426. Thereby, forward movement of the electronic component 426 may be resisted by the electronic component terminal 452 and the tab 480 of the first heating terminal 448. Conversely, rearward movement of the electronic component 426 may be resisted by the primary surface support sections 478 of the heating terminals 448, 450.

However, as described hereinafter, in other embodiments the electronic component may be positioned and supported in differing manners. In this regard, FIG. 10 illustrates a cartridge 504 according to an additional example embodiment of the present disclosure. As illustrated, the cartridge 504 may include an outer body 516 and a base 532 coupled to one end of the outer body. A mouthpiece 546 may be engaged with an end of the outer body 516 opposite from the base 532. The mouthpiece 546 may define a mouth opening as described above.

A heating element 522 may be positioned within the outer body 516. A first heating terminal 548 and a second heating terminal 550 may be coupled to the heating element 522. An electronic component 526 may be received in the outer body 516. An electronic component terminal 552 (see, FIG. 12) may engage the electronic component 526. Further, the terminals 548, 550, 552 may extend into the base 532 to allow for electrical connectivity with a control body as described above.

Additionally, the cartridge 504 may include a unitary reservoir and liquid transport element 554 that contains an aerosol precursor composition. The unitary reservoir and liquid transport element 554 may extend between a base end 560 and a mouthpiece end 562. The unitary reservoir and liquid transport element 554 may define a protrusion 564 about which the heating element 522 may at least partially extend in contact therewith.

As illustrated in FIG. 11, the unitary reservoir and liquid transport element 554 may include one or more channels 555 extending at least partially therethrough. The channels 555 may define a first groove 568 and a second groove 570. As illustrated in FIG. 10, the first heating terminal 548 and the second heating terminal 550 may respectively extend in the first groove 568 and the second groove 570. Thus, the heating terminals 548, 550 may be at least partially received in the channels 555. The unitary reservoir and liquid transport element 554 may comprise a porous monolith such as a porous glass or porous ceramic, and in some embodiments the unitary reservoir and liquid transport element may define a variable porosity.

Thus, the cartridge 504 may be substantially similar to the cartridge 304 of FIG. 4 in a number of respects. Accordingly, for brevity purposes, particular details of the cartridge 504 shared with the cartridge 304 of FIG. 4 will not be repeated. However, the cartridge 504 may differ in one or more respects.

As illustrated in FIG. 10, the electronic component 526 may be positioned between the base 532 and the unitary reservoir and liquid transport element 554. In this regard, a longitudinal axis of the electronic component 526 may extend substantially perpendicular to a longitudinal axis of the outer body 516. Further, as illustrated in FIG. 12, the first heating terminal 548 and the second heating terminal 550 may extend substantially perpendicular to the longitudinal axis of the electronic component 526. In this regard, as noted above with respect to FIG. 10, the heating terminals 548, 550 may be received in the grooves 568, 570 defined in the unitary reservoir and liquid transport element 554. However, as illustrated in FIG. 12, the first heating terminal 548 may define a tab 548A and the second heating terminal 550 may define a tab 550A that extend laterally therefrom. The tabs 548A, 550A and the electronic component terminal 552 may engage a major surface of the electronic component 526. Thereby, the tabs 548A, 550A defined by the heating terminals 548, 550 and the electronic component terminal 552 may press the electronic component 526 against the base 532, such that the electronic component is retained in place.

Further, the electronic component 526 may include a plurality of contacts. The tab 548A of the first heating terminal 548 may engage a first contact 582A. The tab 550A of the second heating terminal 550 may engage a second contact 582B. Further, the electronic component terminal 552 may engage a third contact 582C. In this regard, the heating terminals 548, 550 may supply electrical power to the electronic component 526 and the electronic component terminal may establish an electrical connection with the electronic component such that data may be transferred between the cartridge 504 (see, FIG. 10) and a control body as described above.

With reference to FIG. 10, airflow may define a flow path through the base 532, past the electronic component 526, around the unitary reservoir and liquid transport element 554 through the grooves 568, 570, past the heating element 522 at which vapor is added thereto, and out the mouthpiece 546 through the mouth opening. Thus, the airflow may be directed through the channels 555 (see, FIG. 11) extending at least partially through the unitary reservoir and liquid transport element 554. Thereby, the flow path may generally extend beside, rather than along the electronic component 526. In this regard, the electronic component 526 may define a semi-circular shape and the longitudinal axis thereof may extend substantially perpendicular to a longitudinal axis of the outer body 516, such that the air flow may extend beside, rather than through or along the electronic component. Thus, the electronic component 526 may be substantially removed from the air flow path through the cartridge 504.

In an additional embodiment a method for producing a vapor is provided. As illustrated in FIG. 13, the method may include containing an aerosol precursor composition in a unitary reservoir and liquid transport element at operation 602. Further, the method may include vaporizing at least a portion of the aerosol precursor composition at the unitary reservoir and liquid transport element at operation 604.

In some embodiments vaporizing at least the portion of the aerosol precursor composition at the unitary reservoir and liquid transport element at operation 604 may comprise directing an electrical current to a heating element substantially surrounded by the unitary reservoir and liquid transport element. In another embodiment vaporizing at least the portion of the aerosol precursor composition at the unitary reservoir and liquid transport element at operation 604 may comprise directing an electrical current to a heating element extending around at least a portion of the unitary reservoir and liquid transport element. The method may further include directing an airflow through one or more channels extending at least partially through the unitary reservoir and liquid transport element. Further, containing the aerosol precursor composition in the unitary reservoir and liquid transport element at operation 602 may comprise containing the aerosol precursor composition in an integral porous monolith.

In an additional embodiment a method for producing an aerosol delivery device is provided. The method may include forming a unitary reservoir and liquid transport element from a porous monolithic material. Further, the method may include positioning a heating element and the unitary reservoir and liquid transport element in an outer body such that the heating element is proximate the unitary reservoir and liquid transport element. The method may additionally include dispensing an aerosol precursor composition into the unitary reservoir and liquid transport element.

In some embodiments forming the unitary reservoir and liquid transport element may comprise injection molding the unitary reservoir and liquid transport element. The method may further include engaging a first heating terminal and a second heating terminal with the heating element. Forming the unitary reservoir and liquid transport element from the porous monolithic material may comprise insert molding at least one of the heating element, the first heating terminal, and the second heating terminal into the unitary reservoir and liquid transport element. Further, in some embodiments forming the unitary reservoir and liquid transport element from a porous monolithic material may comprise forming the unitary reservoir and liquid transport element from a porous ceramic.

As described above, embodiments of the present disclosure include a unitary reservoir and liquid transport element formed from an integral porous monolith. However, as described hereinafter, in other embodiments the liquid transport element and the reservoir may be provided as separate elements.

In this regard, FIG. 14 illustrates a cartridge 704 according to an additional example embodiment of the present disclosure. As illustrated, the cartridge 704 may include an outer body 716 and a base 732 coupled to one end of the outer body. A mouth opening 724 may be positioned at an opposing end of the outer body 716. A heating element 722 may be positioned within the outer body 716. As illustrated, in one embodiment a longitudinal axis of the heating element 722 may be substantially parallel to a longitudinal axis of the outer body 716.

The mouth opening 724 may be defined in a mouthpiece 746, which may be engaged with an end of the outer body 716 opposite from the base 732. A first heating terminal 748 and a second heating terminal 750 may be coupled to the heating element 722. An electronic component 726 may be positioned between the first heating terminal 748 and the second heating terminal 750. A longitudinal axis of the electronic component 726 may extend substantially parallel to a longitudinal axis of the outer body 716. An electronic component terminal 752 may engage the electronic component 726 as described above and illustrated, for example, in FIG. 9. Further, the terminals 748, 750, 752 may extend into the base 732 to allow for electrical connectivity with a control body as described above. In this regard, the terminals, the electronic component, and the base may be substantially similar to, or the same as the corresponding elements in FIG. 9.

Additionally, the cartridge 704 may include a reservoir 718 received in the outer body 716. The reservoir 718 may contain an aerosol precursor composition. The reservoir 728 may define a tubular configuration. The reservoir 718 may extend between a base end 718a and a mouthpiece end 718b.

The cartridge 704 may further include a liquid transport element 720. The liquid transport element 720 may extend between a base end 720a and a mouthpiece end 720b. Further, the liquid transport element 720 may extend between the reservoir 718 and the heating element 722. In this regard, the liquid transport element 720 may be at least partially received in and surrounded by the reservoir 718.

One or both of the reservoir 718 and the liquid transport element 720 may comprise a porous monolith such as a porous glass or porous ceramic. In one example embodiment the liquid transport element 720 may comprise a porous monolith and the reservoir 718 may comprise a fibrous mat (e.g., cellulose acetate), which may be wrapped thereabout. In some embodiments the liquid transport element 720 may be relatively more porous than the reservoir 718. In this regard, the liquid transport element 720 may be configured to draw the aerosol precursor composition retained in the reservoir 718 to the heating element 722. Further, in some embodiments one or both of the reservoir 718 and the liquid transport element 720 may define a variable porosity.

FIG. 15 illustrates the liquid transport element 720. As illustrated, the liquid transport element 720 may define at least one channel 755 extending at least partially therethrough. The channel 755 may include a first section 756 and a second section 766. The first section 756 of the channel 755 may extend from the mouthpiece end 720b of the liquid transport element 720 to the second section 766 of the channel. The second section 766 of the channel 755 may extend from the first section 756 of the channel to the base end 720a of the liquid transport element 720.

The electronic component 726 may be at least partially positioned inside the liquid transport element 720. In this regard, the electronic component 726 may be received in the second section 766 of the channel 755. Further, the heating element 722 may be at least partially positioned inside the liquid transport element 720. In this regard, the heating element 722 is positioned in the first section 756 of the channel 755 and in contact therewith in the illustrated embodiment.

Additionally, as illustrated in FIG. 14, one or both of the first heating terminal 748 and the second heating terminal 750 may at least partially extend through the liquid transport element 720. In this regard, the first heating terminal 748 and the second heating terminal 750 may extend from the base 732 through the second section 766 of the channel 755 to the heating element 722 at the first section 756 of the channel. A longitudinal axis of the liquid transport element 720 may be substantially parallel to a longitudinal axis of the first heating terminal 748 and a longitudinal axis of the second heating terminal 750.

Airflow may define a flow path through the base 732, into the second section 766 of the channel 755 through the liquid transport element 720, past the electronic component 726, past the heating element 722 in the first section 756 of the channel at which vapor is added thereto, and out the mouthpiece 746 through the mouth opening 724. In this regard, the liquid transport element 720 may define a flow director that directs the air to the heating element 722 at which the vapor is produced. Accordingly, usage of a separate flow director may not be required.

Regarding the production of vapor, the reservoir 718 may contain the aerosol precursor composition. The liquid transport element 720 may be in contact with the reservoir 718 along substantially the entirety of the length thereof. Further, the liquid transport element 720 may extend around all or a part of the inner circumference of the reservoir 718. For example, in the illustrated embodiment the liquid transport element 720 is in contact with an entirety of an inner circumference of the aperture 784 defined by the reservoir 718 at the mouthpiece end 720b. By providing a relatively large area of contact between the reservoir 718 and the liquid transport element 720, fluid transmission from the reservoir to the liquid transport element 720 may be improved. Similarly, the liquid transport element 720 may substantially surround the heating element 722 to provide for improved vapor production FIGS. 16 and 17 illustrate a cartridge 804 according to an additional example embodiment of the present disclosure. As illustrated, the cartridge 804 may include an outer body 816 and a base 832 coupled to one end of the outer body. A mouth opening may be defined in a mouthpiece 846, which may be engaged with an end of the outer body 816 opposite from the base 832. A heating element 822 may be positioned within the outer body 816. As illustrated, in one embodiment a longitudinal axis of the heating element 822 may be substantially parallel to a longitudinal axis of the outer body 816.

A first heating terminal 848 and a second heating terminal 850 may be coupled to the heating element 822. An electronic component 826 (see, FIGS. 17 and 18) may be positioned between the first heating terminal 848 and the second heating terminal 850. A longitudinal axis of the electronic component 826 may extend substantially parallel to a longitudinal axis of the outer body 816 as described and illustrated above, by way of example, with respect to FIG. 14. An electronic component terminal 852 may engage the electronic component 826 as described above and illustrated, for example, in FIG. 9. Further, the terminals 848, 850, 852 may extend into the base 832 to allow for electrical connectivity with a control body as described above. In this regard, the terminals, the electronic component, and the base may be substantially similar to, or the same as the corresponding elements in FIG. 9.

Additionally, the cartridge 804 may include a reservoir 818 received in the outer body 816. The reservoir 818 may contain an aerosol precursor composition. The reservoir 818 may extend between a base end 818a and a mouthpiece end 818b. The reservoir 818 may define a tubular configuration and include an aperture 884 extending therethrough, as illustrated in FIG. 17.

The cartridge 804 may further include a liquid transport element 820. The liquid transport element 820 may extend between a base end 820a and a mouthpiece end 820b. Further, the liquid transport element 820 may extend between the reservoir 818 and the heating element 822 in order to transport the aerosol precursor composition from the reservoir to the heating element. In this regard, the liquid transport element 820 may be at least partially received in the aperture 884 (see, FIG. 17) defined through the reservoir 818.

One or both of the reservoir 818 and the liquid transport element 820 may comprise a porous monolith such as a porous glass or porous ceramic. In one example embodiment the liquid transport element 820 may comprise a porous monolith and the reservoir 818 may comprise a fibrous mat (e.g., cellulose acetate), which may be wrapped thereabout. In some embodiments the liquid transport element 820 may be relatively more porous than the reservoir 818. In this regard, the liquid transport element 820 may be configured to draw the aerosol precursor composition retained in the reservoir 818 to the heating element 822. Further, in some embodiments one or both of the reservoir 818 and the liquid transport element 820 may define a variable porosity.

As illustrated in FIG. 16, the heating element 822 may extend at least partially about the liquid transport element 820. More particularly, the liquid transport element 820 may define a protrusion 864, which may be located at a distal end of the liquid transport element. In this embodiment the protrusion 864 may be positioned at the mouthpiece end 820b of the liquid transport element 820. As illustrated in FIG. 16, the heating element 822 may extend at least partially about the protrusion 864 and in contact therewith.

As illustrated in FIG. 18, the liquid transport element 820 may define one or more channels 855 extending at least partially therethrough. The one or more channels 855 may include a slot 866. As schematically illustrated, the electronic component 826 may be received in the one or more channels 855 at the slot 866. Further, the one or more channels 855 defined in the liquid transport element 820 may include a first terminal groove 868 (see, FIG. 17) and a second terminal groove 870. The protrusion 864 may extend from the mouthpiece end 820b of the liquid transport element 820 to the terminal grooves 868, 870. The terminal grooves 868, 870 may extend on each side of the liquid transport element 820 between the protrusion 864 and the slot 866. The slot 866 may extend from the terminal grooves 868, 870 to the base end 820a of the liquid transport element 820.

As illustrated in FIGS. 16 and 17, the heating terminals 848, 850 may extend through the one or more channels 855 (see, FIG. 18) at the slot 866 and the terminal grooves 868, 870. In this regard, the first heating terminal 848 and the second heating terminal 850 may be positioned between the liquid transport element 820 and the reservoir 818. A longitudinal axis of the liquid transport element 820 may be substantially parallel to a longitudinal axis of the first heating terminal 848 and a longitudinal axis of the second heating terminal 850.

As noted above, the electronic component 826 (see, e.g., FIGS. 17 and 18) may be at least partially positioned inside the liquid transport element 820. In this regard, the electronic component 826 may be received in the one or more channels 855 at the slot 866 between the first heating terminal 848 and the second heating terminal 850.

Further, the channels 855 defined in the liquid transport element 820 may include one or more airflow grooves. In the illustrated embodiment, the liquid transport element 820 defines a first airflow groove 886 and a second airflow groove 888. The airflow grooves 886, 888 may be positioned between the terminal grooves 868, 870 and extend along the longitudinal length of the liquid transport element 820 at the outer surface thereof. In this regard, airflow may define a flow path through the base 832, around the liquid transport element 820 through the airflow grooves 886, 888, past the heating element 822 at which vapor is added thereto, and out the mouthpiece 846 through the mouth opening. Accordingly, usage of a separate flow director may not be required.

Regarding the production of vapor, the reservoir 818 may contain the aerosol precursor composition. The liquid transport element 820 may be in contact with the reservoir 818 along substantially the entirety of the length thereof other than at the protrusion 864. Further, the liquid transport element 820 may contact a relatively large portion of the inner circumference of the aperture 884 extending through the reservoir 818 (e.g., about half thereof at the base end 820a in the illustrated embodiment, as illustrated in FIG. 17). By providing a relatively large area of contact between the reservoir 818 and the liquid transport element 820, fluid transmission from the reservoir to the liquid transport element may be improved. Similarly, the heating element 822 may substantially surround the liquid transport element 820 at the protrusion 864 to provide for improved vapor production FIGS. 19 and 20 illustrate a cartridge 904 according to an additional example embodiment of the present disclosure. As illustrated, the cartridge 904 may include an outer body 916 and a base 932 coupled to one end of the outer body. A mouth opening 924 may be defined in a mouthpiece 946, which may be engaged with an end of the outer body 916 opposite from the base 932. A heating element 922 may be positioned within the outer body 916. As illustrated, in one embodiment a longitudinal axis of the heating element 922 may be substantially parallel to a longitudinal axis of the outer body 916.

A first heating terminal 948 and a second heating terminal 950 may be coupled to the heating element 922. An electronic component 926 (see, FIG. 19) may be received in the outer body 916. A longitudinal axis of the electronic component 926 may extend substantially perpendicular to a longitudinal axis of the outer body 916. Further, the first heating terminal 948 and the second heating terminal 950 may extend substantially perpendicular to the longitudinal axis of the electronic component 926. The heating terminals 948, 950 and an electronic component terminal may engage the electronic component 926 and extend into the base 932 to allow for electrical connectivity with a control body as described above. In this regard, the terminals, the base and the electronic component of FIG. 19 may be substantially similar to, or the same as, the terminals, the base and the electronic component illustrated in FIG. 12. Accordingly, details with respect to these components and the functions performed thereby will not be repeated for brevity purposes.

Additionally, the cartridge 904 may include a reservoir 918 received in the outer body 916. The reservoir 918 may contain an aerosol precursor composition. The reservoir 918 may extend between a base end 918a and a mouthpiece end 918b. The electronic component 926 may be positioned between the base end 918a of the reservoir 918 and the base 932. The reservoir 918 may define a substantially tubular configuration and include an aperture 984 extending therethrough (see, FIG. 20).

The cartridge 904 may further include a liquid transport element 920. The liquid transport element 920 may extend between a base end 920a and a mouthpiece end 920b. The electronic component 926 may be positioned between the base end 920a and the base 932. Further, the liquid transport element 920 may extend between the reservoir 918 and the heating element 922 in order to transport the aerosol precursor composition from the reservoir to the heating element. In this regard, the liquid transport element 920 may be at least partially received in the aperture 984 defined through the reservoir 918. For example, the liquid transport element 920 may define a cylindrical configuration, with a protrusion 964 extending outwardly therefrom at the mouthpiece end 920b.

One or both of the reservoir 918 and the liquid transport element 920 may comprise a porous monolith such as a porous glass or porous ceramic. In one example embodiment the liquid transport element 920 may comprise a porous monolith and the reservoir 918 may comprise a fibrous mat (e.g., cellulose acetate), which may be wrapped thereabout. In some embodiments the liquid transport element 920 may be relatively more porous than the reservoir 918. In this regard, the liquid transport element 920 may be configured to draw the aerosol precursor composition retained in the reservoir 918 to the heating element 922. Further, in some embodiments one or both of the reservoir 918 and the liquid transport element 920 may define a variable porosity.

As illustrated in FIG. 19, the heating element 922 may extend at least partially about the liquid transport element 920. More particularly, the heating element 922 may extend at least partially about the protrusion 964, at which the liquid transport element 920 extends out from the aperture 984 (see, FIG. 20) defined through the reservoir 918, and in contact therewith.

As illustrated in FIG. 20, the heating terminals 948, 950 may extend through the aperture 984 defined through the reservoir 918. In this regard, the first heating terminal 948 and the second heating terminal 950 may be positioned beside the liquid transport element 920 within the aperture 984. A longitudinal axis of the liquid transport element 920 may be substantially parallel to a longitudinal axis of the first heating terminal 948 and a longitudinal axis of the second heating terminal 950.

In some embodiments airflow may define a flow path through the base 932, through the aperture 984 through the reservoir 918, past the heating element 922 at which vapor is added thereto, and out the mouthpiece 946 through the mouth opening 924. However, in other embodiments airflow may additionally or alternatively define a flow path through the base 932, around the reservoir 918, past the heating element 922 at which vapor is added thereto, and out the mouthpiece 946 through the mouth opening 924.

In each of these embodiments, usage of a separate flow director through which the air flows may not be required. However, as illustrated in FIGS. 19 and 20, the cartridge 904 may further comprise a reservoir tube 990. The reservoir tube 990 may surround the reservoir 918 such that the airflow is directed between the reservoir tube 990 and the outer body 916. In this regard, the reservoir tube 990 may be configured to retain the reservoir 918 in a tubular configuration and separate the reservoir from the outer body 916 to allow airflow therebetween.

Regarding the production of vapor, the reservoir 918 may contain the aerosol precursor composition. The liquid transport element 920 may be in contact with the reservoir 918 along substantially the entirety of the length thereof other than at the protrusion 964. Further, the liquid transport element 920 may contact a relatively large portion of the inner circumference of the reservoir 918 as illustrated in FIG. 20. By providing a relatively large area of contact between the reservoir 918 and the liquid transport element 920, fluid transmission from the reservoir to the liquid transport element may be improved. Similarly, the heating element 922 may substantially surround the liquid transport element 920 at the protrusion 964 to provide for improved vapor production.

FIGS. 21 and 22 illustrate a cartridge 1004 according to an additional example embodiment of the present disclosure. As illustrated, the cartridge 1004 may include an outer body 1016 and a base 1032 coupled to one end of the outer body. A mouth opening 1024 may be defined in a mouthpiece 1046, which may be engaged with an end of the outer body 1016 opposite from the base 1032. A heating element 1022 may be positioned within the outer body 1016. As illustrated, in one embodiment a longitudinal axis of the heating element 1022 may be substantially parallel to a longitudinal axis of the outer body 1016.

A first heating terminal 1048 and a second heating terminal 1050 may be coupled to the heating element 1022. An electronic component 1026 may be received in the outer body 1016. A longitudinal axis of the electronic component 1026 may extend substantially perpendicular to a longitudinal axis of the outer body 1016. Further, the first heating terminal 1048 and the second heating terminal 1050 may extend substantially perpendicular to the longitudinal axis of the electronic component 1026. The heating terminals 1048, 1050 and an electronic component terminal may engage the electronic component 1026 and extend into the base 1032 to allow for electrical connectivity with a control body as described above. In this regard, the terminals, the base and the electronic component of FIG. 21 may be substantially similar to, or the same as, the terminals, the base and the electronic component illustrated in FIG. 12. Accordingly, details with respect to these components and the functions performed thereby will not be repeated for brevity purposes.

Additionally, the cartridge 1004 may include a reservoir 1018 received in the outer body 1016. The reservoir 1018 may contain an aerosol precursor composition. The reservoir 1018 may extend between a base end 1018*a* and a mouthpiece end 1018*b*. The electronic component 1026 may be positioned between the base end 1018*a* of the reservoir 1018 and the base 1032. The reservoir 1018 may define a modified tubular configuration including an opening 1084 extending therethrough (see, FIG. 22).

The cartridge 1004 may further include a liquid transport element 1020. The liquid transport element 1020 may extend between a base end positioned proximate the base 1032 and a mouthpiece end positioned proximate the mouthpiece 1046. The electronic component 1026 may be positioned between the base end of the liquid transport element 1020 and the base 1032. Further, the liquid transport element 1020 may extend between the reservoir 1018 and the heating element 1022 in order to transport the aerosol precursor composition from the reservoir to the heating element. In this regard, the liquid transport element 1020 may be at least partially received in the opening 1084 defined through the reservoir 1018. For example, the liquid transport element 1020 may define a cylindrical configuration, with a protrusion 1064 extending outwardly therefrom at the mouthpiece end thereof.

One or both of the reservoir 1018 and the liquid transport element 1020 may comprise a porous monolith such as a porous glass or porous ceramic. In one example embodiment the liquid transport element 1020 may comprise a porous monolith and the reservoir 1018 may comprise a fibrous mat (e.g., cellulose acetate), which may be wrapped thereabout. In some embodiments the liquid transport element 1020 may be relatively more porous than the reservoir 1018. In this regard, the liquid transport element 1020 may be configured to draw the aerosol precursor composition retained in the reservoir 1018 to the heating element 1022. Further, in some embodiments one or both of the reservoir 1018 and the liquid transport element 1020 may define a variable porosity.

As illustrated in FIG. 21, the heating element 1022 may extend at least partially about the liquid transport element 1020. More particularly, the heating element 1022 may extend at least partially about the protrusion 1064, at which the liquid transport element 1020 extends out from the opening 1084 (see, FIG. 22) defined through the reservoir 1018, and in contact therewith.

As illustrated in FIG. 22, the heating terminals 1048, 1050 may extend through the opening 1084 defined through the reservoir 1018. In this regard, the first heating terminal 1048 and the second heating terminal 1050 may be positioned beside the liquid transport element 1020 within the opening 1084. A longitudinal axis of the liquid transport element 1020 may be substantially parallel to a longitudinal axis of the first heating terminal 1048 and a longitudinal axis of the second heating terminal 1050.

Further, the cartridge 1004 may include a flow director 1092. The flow director 1092, which may be tubular, may extend through the reservoir 1018. The flow director 1092 may be received in the opening 1084 extending through the reservoir 1018 as illustrated in FIG. 22, or the flow director may be received in a separate aperture extending therethrough. The flow director 1092 may define a longitudinal axis extending substantially parallel to a longitudinal axis of the liquid transport element 1020 and substantially parallel to a longitudinal axis of the outer body 1016. However, as illustrated in FIG. 22, the flow director 1092 may be offset from a central longitudinal axis of the outer body 1016 and positioned beside the liquid transport element 1020.

Thereby, in some embodiments airflow may define a flow path through the base 1032, through the flow director 1092, past the heating element 1022 at which vapor is added thereto, and out the mouthpiece 1046 through the mouth opening 1024. Accordingly, in some embodiments a separate flow director may be employed to direct airflow as desired.

Regarding the production of vapor, the reservoir 1018 may contain the aerosol precursor composition. The liquid transport element 1020 may be in contact with the reservoir 1018 along substantially the entirety of the length thereof other than at the protrusion 1064. Further, the liquid transport element 1020 may contact a relatively large portion of the inner surface of the reservoir 1018 as illustrated in FIG. 22. By providing a relatively large area of contact between the reservoir 1018 and the liquid transport element 1020, fluid transmission from the reservoir to the liquid transport element may be improved. Similarly, the heating element 1022 may substantially surround the liquid transport element 1020 at the protrusion 1064 to provide for improved vapor production.

In an additional embodiment a method for producing an aerosol delivery device is provided. As illustrated in FIG. 23, the method may include positioning a heating element, a reservoir and a liquid transport element in an outer body such that the liquid transport element is in contact with the reservoir and the heating element at operation 1102. Positioning the heating element, the reservoir and the liquid transport element in the outer body at operation 1102 may include aligning a respective longitudinal axis of the heating element, the reservoir and the liquid transport element at operation 1103.

In some embodiments the method may further include positioning the liquid transport element at least partially within the reservoir. Positioning the liquid transport element at least partially within the reservoir may include wrapping the liquid transport element with the reservoir. The method may additionally include inserting the heating element into a channel extending at least partially though the liquid transport element. In another embodiment the method may further include coupling the heating element an outer surface of the liquid transport element.

In an additional embodiment a method for producing an aerosol delivery device is provided. The method may include forming a liquid transport element from a porous monolithic material. Further, the method may include positioning a heating element, a reservoir and the liquid transport element in an outer body such that the liquid transport element is in contact with the reservoir and the heating element is proximate the liquid transport element. The method may additionally include dispensing an aerosol precursor composition into the reservoir.

In some embodiments forming the liquid transport element may comprise injection molding the liquid transport element. The method may further include engaging a first heating terminal and a second heating terminal with the heating element. Forming the liquid transport element from the porous monolithic material may include insert molding at least one of the heating element, the first heating terminal, and the second heating terminal into the liquid transport element. Additionally, forming the liquid transport element from the porous monolithic material may comprise forming the liquid transport element from a porous ceramic.

As noted herein elements of the cartridges of the present disclosure may comprise a porous monolith. In this regard, the unitary reservoir and liquid transport elements, the reservoirs, and/or the liquid transport elements of the present disclosure may comprise a porous monolith. The porous monoliths may be shape-stable, which may thereby facilitate assembly of the cartridges. For example, the porous monoliths may be substantially rigid. Further, shape-stable porous monoliths may be suitable for directing airflow through the cartridge. By way of contrast, embodiments of the liquid transport elements formed from fiberglass and reservoirs formed from cellulose acetate may be flexible and the shape thereof may change when contacted, such that assembly of cartridges including such components may be relatively more difficult and such components may not be suitable for directing airflow due to pressure changes within the cartridge potentially altering the shape thereof. Further, components comprising a porous monolith may be molded or otherwise formed to define shapes that may be difficult to form from materials that are flexible.

As further noted herein, each of the porous monoliths disclosed herein may define a variable porosity. Usage of a variable porosity may be employed to store and direct the aerosol precursor composition to desired locations within the porous monoliths. For example, a relatively higher porosity may be employed at locations at which fluid storage or transport therethrough is desired. Conversely, a relatively lesser porosity may be employed at locations at which leakage from the porous monolith is a greater concern. Thus, for example, in embodiments of the cartridge including the unitary reservoir and liquid transfer element, a relatively more porous region may be configured to store and direct the aerosol precursor composition to the heating element. In embodiments of the cartridge including a reservoir and a liquid transport element as separate elements, a relatively more porous region in the reservoir may be configured to store and draw the aerosol precursor composition to the liquid transport element. Additionally or alternatively, a relatively more porous region in the liquid transport element may be configured to draw the aerosol precursor composition within the liquid transport element to the heating element. In this regard, the aerosol precursor composition may flow relatively more easily through portions of the porous monoliths defining a relatively greater porosity.

Accordingly, one or more regions of the porous monoliths may define a relatively greater porosity in order to accommodate storage and encourage movement of the aerosol precursor composition therethrough. Such regions may extend along at least a portion of the longitudinal length of the porous monoliths to thereby facilitate movement of the aerosol precursor composition toward the heating element, which may be positioned proximate an end thereof. Further such regions of relatively greater porosity may be partially or fully surrounded by a region having a relatively lesser porosity in order to resist leakage of the aerosol precursor composition from the porous monolith. In some embodiments the portion of the porous monolith most susceptible to leakage may be the region exposed to airflow through the cartridge, which may be proximate the heating element. Thus, the porous monolith may include relatively smaller pores proximate the heating element, whereas the porous monolith may include relatively larger pores proximate the reservoir. This porosity gradient will naturally pull liquid aerosol precursor composition from the larger pore areas to the smaller pore areas. Accordingly by varying the porosity of the porous monolith, the fluid storage and transport characteristics thereof may vary depending on a location therein.

Further, usage of cartridges configured as described herein may provide benefits in terms of increased aerosol precursor composition capacity for a given cartridge size. For example, the cartridge 104 illustrated in FIG. 1 may have a total aerosol precursor composition capacity of approximately 0.6 cubic centimeters (cc) for the liquid transport element 120 and the reservoir 118. However, usage of a liquid transport element, reservoir, or unitary reservoir and liquid transport element comprising a porous monolith may provide for increased aerosol precursor composition capacity in a cartridge having substantially identical outer dimensions. In this regard, the embodiments of cartridges 204, 304, 404, 504, 704, 804, 904, 1004 illustrated in FIGS. 2, 4, 6, 10, 14, 16, 19, and 21 may have total aerosol precursor composition capacities of 1.1 cc, 0.9 cc, 1.1 cc, 1.0 cc, 1.1 cc, 1.1 cc, 0.9 cc, and 1.1 cc, respectively. In this regard, in the embodiments of cartridges disclosed herein, the usage of the space within the outer body at which the aerosol precursor composition is received is maximized.

Further, usage of cartridges configured as described herein may provide benefits in terms of improved vapor production. In this regard, whereas the heating element 122 included in the cartridge 104 of FIG. 1 includes relatively small coils in view of the liquid transport element 120 defining a relatively small diameter, the heating elements of the cartridges 204, 304, 404, 504, 704, 804, 904, 1004 illustrated in FIGS. 2, 4, 6, 10, 14, 16, 19, and 21 may be approximately twice as long in terms of the length of the wire defining the heating elements. In this regard, the liquid transport element or unitary reservoir and liquid transport element may define increased internal or external dimension configured to receive the relatively larger heating element. Usage of a relatively larger heating element may allow for the production of a larger amount of heat, thereby allowing for more rapid production of vapor and/or a larger quantity thereof.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An atomizer for an aerosol delivery device, the atomizer comprising:
 a porous monolith formed of a ceramic and comprising a first end and an opposing second end, wherein a reservoir defining a channel is arranged proximate the opposing second end and extending toward the first end and only partially through the porous monolith from an exterior surface of the second end of the porous monolith, the reservoir being configured to retain an aerosol precursor composition along the channel, and comprising a liquid transport element in contact with the channel of the reservoir along a substantial entirety thereof and being configured to transport the aerosol precursor composition through a portion of the liquid transport element; and
 a vaporization element positioned relative to the porous monolith so as to be configured for vaporization of the aerosol precursor composition;
 wherein at least a portion of the first end of the ceramic monolith is substantially planar, and the vaporization element is at least partially positioned on the substantially planar portion of the ceramic monolith.

2. The atomizer according to claim 1, wherein the porous monolith has a substantially square or substantially rectangular cross-section.

3. The atomizer according to claim 1, wherein the vaporization element is a heater.

4. An aerosol delivery device comprising:
 an outer housing;
 a porous monolith formed of a ceramic and comprising a first end and an opposing second end, and being positioned within the outer housing, a reservoir defining a channel being arranged proximate the opposing second end and extending toward the first end and only partially through the porous monolith from an exterior surface of the second end of the porous monolith, the reservoir being configured to retain an aerosol precursor composition along the channel, and comprising a liquid transport element in contact with the channel of the reservoir along a substantial entirety thereof and being configured to transport the aerosol precursor composition through a portion of the liquid transport element;
 a vaporization element positioned within the outer housing relative to the porous monolith so as to be configured for vaporization of the aerosol precursor composition to form a vapor;
 wherein at least a portion of the first end of the ceramic monolith is substantially planar, and the vaporization element is at least partially positioned on the substantially planar portion of the ceramic monolith.

5. The aerosol delivery device according to claim 4, further comprising an air entry, a mouth end, and an aerosol port formed in the mouth end.

6. The aerosol delivery device according to claim 5, wherein an air flow passing between the air entry and the aerosol port is configured to pass substantially across a surface of the porous monolith.

7. The aerosol delivery device according to claim 4, wherein the porous monolith has a substantially square or substantially rectangular cross-section.

8. The aerosol delivery device according to claim 4, wherein the vaporization element is a heater.

\* \* \* \* \*